US 6,884,356 B2

(12) United States Patent
Kosenka et al.

(10) Patent No.: US 6,884,356 B2
(45) Date of Patent: Apr. 26, 2005

(54) LOW-LEVEL BORON DETECTION AND MEASUREMENT

(75) Inventors: Paul P. Kosenka, Denver, CO (US); Kevin J. O'Neill, Boulder, CO (US); Richard D. Godec, Longmont, CO (US)

(73) Assignee: Sievers Instruments, Inc., Boulder, CO (US)

( * ) Notice: Subject to any disclaimer, the term of this patent is extended or adjusted under 35 U.S.C. 154(b) by 230 days.

(21) Appl. No.: 10/333,434

(22) PCT Filed: Aug. 4, 2001

(86) PCT No.: PCT/US01/24637

§ 371 (c)(1),
(2), (4) Date: Jan. 21, 2003

(87) PCT Pub. No.: WO02/12129

PCT Pub. Date: Feb. 14, 2002

(65) Prior Publication Data

US 2004/0020840 A1 Feb. 5, 2004

Related U.S. Application Data

(60) Provisional application No. 60/223,474, filed on Aug. 7, 2000.

(51) Int. Cl.[7] .............................. C02F 1/42; G01N 27/06
(52) U.S. Cl. ..................... 210/662; 210/746; 210/96.1; 210/900; 436/150; 436/182; 324/441

(58) Field of Search ................................. 210/638, 662, 210/742, 746, 96.1, 900; 324/441; 436/150, 182; 702/25

(56) References Cited

U.S. PATENT DOCUMENTS

| | | | |
|---|---|---|---|
| 3,468,764 A | 9/1969 | Cohen et al. |
| 3,597,613 A | 8/1971 | Rajagopal |
| 4,081,683 A | 3/1978 | Csom et al. |
| 4,204,259 A | 5/1980 | Yabe |
| 5,833,846 A | 11/1998 | Tanabe et al. |

FOREIGN PATENT DOCUMENTS

JP          10-62371          3/1998

*Primary Examiner*—Robert A. Hopkins
(74) *Attorney, Agent, or Firm*—David Silverstein; Andover-IP-Law

(57) ABSTRACT

Methods and apparatus (50) are disclosed for accurately measuring low concentrations of boron in deionized water utilizing the chemical reaction of boric acid with a polyol by injecting very small plugs of concentrated polyol into streams of boron containing and non-boron containing water samples to produce an ionized acids product, and then measuring the conductivity difference (delta conductivity), corrected for interfering or extraneous factors which can effect conductivity, between such boron containing and non-boron containing samples using a conductivity and temperature detector (23).

43 Claims, 7 Drawing Sheets

LOW-LEVEL BORON DETECTION AND MEASUREMENT

This application claims the benefit of Provisional application Ser. No. 60/223,474, filed Aug. 7, 2000.

The present invention relates generally to methods and apparatus for detecting and measuring low concentrations of boron in deionized water based on the reaction of boric acid with well-known polyols to form well ionized complexes. The formation of such well ionized complexes causes dramatic increases in the conductivities of the deionized water, which increases have been found to be mathematically correlated to the concentrations of boron in the water. The method of this invention particularly includes injecting very small "plugs" or aliquots of concentrated polyol into boron containing and non-boron containing water samples, and measuring the conductivity differential between the boron containing and non-boron containing samples. After correcting for the increase in conductivity attributable to the polyol in accordance with this invention and for temperature, highly accurate measures of low concentrations of boron can be obtained utilizing the method and apparatus of this invention.

BACKGROUND OF THE INVENTION

It has become increasingly important in recent years to be able to detect and measure very low concentrations of boron in deionized water with a high degree of accuracy and high reproducibility of results. For example, in certain industrial applications, such as semiconductor manufacture, even very low levels of boron in deionized water used in manufacturing can significantly and adversely affect the quality and performance of the resulting products.

Large amounts of ultrapure water are required in processes to manufacture semiconductors. Boron is one of the contaminates that must be removed to very low concentrations. Boron is a semiconductor p-type dopant used in manufacture of solid state electronics and functions as a principal charge carrier in a crystal of silicon. Accordingly, boron must not be added inadvertently during the manufacturing process. S. Malhotra et al. reported in "Correlation of Boron Breakthrough versus Resistivity and Dissolved Silica in RO/DI System" (Ultrapure Water, May/June 1996. 13(4): p. 22–26) that boron was the first ion to breakthrough the ion exchange resin beds when they switched to thin-film-composite (TFC) reverse osmosis membranes. The introduction of TFC reverse osmosis (RO) membranes (to replace cellulose acetate RO membranes) was very effective in reducing the silica passage of the RO apparatus. The reduction in boron passage was not as great, however. The first ions to leak from the mixed ion exchange resin beds that follow the usual RO pretreatment are weakly ionized compounds such as silica and boron. With TFC RO membranes, silica passage is much less than boron passage. Boron is therefore often the first ion to breakthrough mixed ion exchange resin beds in water purification systems that use RO TFC pretreatment. This is especially true if the feedwater contains high levels of boron. Adsorption of borate ion on anion exchange resins is the most common method to remove boron from ultrapure water. As the resin begins to become exhausted, however, borate is one of the first ions to leak through. Such borate leakage can rapidly exceed acceptable concentration levels.

Thus, there is a need in semiconductor manufacture and many other applications to be able to monitor very low levels of boron in water quickly, accurately, inexpensively, and while a deionized water stream is on-line. Obtaining reliable measurement of very low levels of boron in water also requires methods and apparatus that eliminate or at least minimize the many possible sources of small errors in conventional approaches, for example, unnecessary possible contamination of samples, sensitivity of readings to flow rate variations, and small changes in aqueous conductivity caused by polyol added to enhance ionization of boric acid. In the past, such small sources of errors have largely been disregarded as insignificant relative to the relatively high concentrations of boron being measured. It will be apparent, however, that as it becomes necessary to measure boron at increasingly lower concentrations, even very small measurement errors inherent in prior art measurement methods become increasingly significant and lead to large measurement distortions on a percentage basis.

It is generally known in the art to form conductive polyol-boron complexes and to utilize conductometric detection techniques. These prior art conductometric polyol-boron complex methods, as well as prior art colorimetric methods, however, are not sensitive enough to detect very low concentrations of boron in purified water used in semiconductor manufacturing. Also, to measure very low levels of boron in water using prior art methods typically requires some form of pre-concentration of boron in the water sample to achieve sensitive enough detection. These added steps introduce additional errors and complexity to the measurement process. Some of these prior art processes for boron detection and their limitations and deficiencies are discussed further below.

One prior art approach to boron measurement is ICP-MS. ICP-MS detection of boron with a pre-concentration step is currently the most sensitive measurement method reported in the literature. The limits of detection are reported to be about 0.005 ppb as B. Without pre-concentration, however, the limit of detection using ICP-MS is much higher, about 0.050 ppb as B. The cost of ICP-MS apparatus is very high, and this fact prevents its common use on-line to measure boron concentrations in real time.

Dionex Corporation has developed an ion chromatographic method to measure boron concentrations. This method uses a styrene-based resin with polyhydroxyl functional groups attached for pre-concentration. The resin polyhydroxyl group-boron complex formation constant is smaller than the boron-mannitol complex formation constant. This allows the resin to collect boron from a water sample; and, after such collection is complete, boron can be removed from the resin using 100 mM mannitol and 2 mM $H_2SO_4$ eluent. The concentrated boron is carried to a resin-packed ion separation column. The separation column resin has an anionic charge. This allows ion exclusion separation of the borate-mannitol anion. Conductometric detection is then used to measure the borate-mannitol complex. The limit of boron detection with the pre-concentration column was reported as 0.050 ppb as B. This system is not well suited for on-line measurement of boron in water, however, due to its complexity. This system of boron analysis was reported at the 1998 SPWCC by B. Newton (SPWCC, pp. 197–216, 1998).

P. Cohen et al. (U.S. Pat. No. 3,468,764) described another design for a boron-in-water analysis method and apparatus. Such device introduces boron-containing water and, periodically, a known boron standard, to a bed of compressed mannitol spheres, and then measures the conductivity of the resulting boron-mannitol complex. The conductivity difference between the water sample and the boron standard is proportional to the concentration of boron in the sample. This device is used in boron concentration ranges commonly found in the nuclear power industry. The detector response is reported to be linear at a first slope over a concentration range of 800 to 3200 ppm and also linear over a concentration range of 0–800 ppm but with a second very different slope. Boron has a high radiation cross section to neutrons and is thus used to control nuclear reactors. There are a number of differences between the Cohen et al. '764 patent and the present invention.

The Cohen et al. device does not take account of the necessity to measure the conductivity of polyol/boron-free water to obtain accurate low level boron measurements. This oversight introduces unacceptable errors into measurement of very low boron concentrations.

The Cohen et al. '764 patent does not compare the conductivity of a polyol/boron-containing sample with the conductivity of a polyol/boron-free sample, a feature that is a key aspect of the present invention.

The Cohen et al. device adds mannitol by flowing the sample or boron standard over a bed of mannitol spheres. By contrast, in a preferred embodiment the present invention injects a small volume of a concentrated, even saturated, polyol solution into a micro stream of a boron-containing sample or a boron-free sample. The Cohen et al. method of polyol addition is sensitive to sample flow rate and to the instant surface area of the mannitol bed. If residence time is too short, the mannitol concentration will change. If flows could be controlled so that mannitol concentration approached saturation, mannitol concentration would then be stable. Such a modification, however, is neither described by Cohen et al. nor compatible with the present design. The Cohen et al. design is in addition generally wasteful of mannitol.

Finally, Cohen et al. do not teach the deionization of polyol solution to remove ions that could contaminate the conductivity of the polyol before its addition to the water sample, thereby again introducing inconsistencies and inaccuracies into the boron measurements.

Ikuo Yabe (U.S. Pat. No. 4,204,259) teaches a device that can be used on the primary cooling water in a pressurized water atomic power plant, and, therefore, is generally concerned with measuring relatively high concentrations of boron. In such patent, a mannitol solution and a boron-containing water sample (or a boron standard) are blended together. The conductivity of such boron-containing water sample (or such boron standard) is measured in a first conductivity cell before mannitol is added. The mannitol/boron-containing sample is passed through a thermal correction device and then into a second conductivity measurement cell. This device measures lithium (Li) with the first conductivity cell and corrects the boron measurement made at the second conductivity cell for the Li conductivity contribution. There are a number of differences between the Yabe '259 patent and the present invention.

Yabe '259 describes an invention that continuously blends mannitol solution with a boron-containing sample (or boron standard). This method of polyol addition is also sensitive to variations between the flow rates of the sample and mannitol streams, and therefore introduces measurements errors.

The Yabe '259 process consumes large amounts of mannitol because of the continuous addition method used. By contrast, the preferred method of polyol addition for the present invention is injection of small aliquots.

Yabe '259 does not account for the necessity of correcting for added conductivity attributable to a polyol/boron-free sample for accurate low level boron measurements. This will introduce unacceptable errors in measurements at low boron concentrations.

The present invention compares the conductivity of a polyol/boron-containing sample with that of a polyol/boron-free sample. Yabe '259 does not teach this critical step for boron measurement.

Finally, Yabe '259 does not teach deionization of polyol solution before its addition to the water sample to remove ions that could contaminate the conductivity of the polyol, thereby again introducing inconsistencies and inaccuracies into boron measurements.

A Russian journal publication entitled "Flow-Injection Determination of Boric Acid"; O. V. Krokhim, et al., *Zhurnal Analiticheskoi Khimii*, Vol. 47, No. 5, pp. 773–775 (May 1992) describes use of a flow injection method to measure high levels of boron in water. The range of boron concentrations that can be measured linearly using this approach is reported to be from 10 ppm B to 16,000 ppm B.

Such method has some superficial similarities to the present invention in that both use a flow injection method for determining concentrations of boron, and both also use, conductivity of a polyol/boron-containing sample water solution as a measure of the amount of boron in solution.

There are a number of critical differences, however, between the method taught by the Russian journal article and the present invention. Because the method described by Krokhim et al. does not measure polyo/boron-free background, it cannot accurately measure boron at very low levels of from 0.01 ppb to 1000 ppb (1 ppm). Furthermore, the method of Krokhim et al. describes a generally linear response range from 10 ppm B to 16,000 ppm B. By contrast, the invention of the present application has a mathematically-correlated response range that starts below 0.05 ppb B and continues up to 1000 ppb B and higher.

The method as practiced by Krokhim et al. consumes large amounts of polyol by injecting a sample into a deionized (DI) water stream and then mixing this resultant stream with another stream of concentrated polyol solution. By contrast, the present invention utilizes small injections of concentrated polyol directly into the deionized water sample, thereby consuming only a small amount of polyol to provide boron concentration measurements. Such improved method, using small amounts of polyol, makes this technique compatible with on-line and compact measurement equipment, something that was virtually impossible to achieve with prior art boron measurement processes. The improved efficiency of reagent consumption with the present invention also leads to lower operating costs and smaller instrument volumes and smaller foot prints in industrial production environments.

The method taught by Krokhim et al. results in a high sensitivity to flow ratio variations of the two main streams. By contrast, the present invention does not have this problem because concentrated polyol solution is injected in very small aliquots into a sample. The mixing ratio is accurately fixed and therefore is independent of the sample flow rate.

Krokhim et al. also do not teach deionizing polyol solution to minimize conductivity background variations which will otherwise lead to measurement inconsistencies and inaccuracies.

Furthermore, Krokhim et al. do not compare the conductivity of an aqueous solution of polyol/boron-containing sample with the conductivity of a polyol/boron-free sample, a step which is critical to the present invention.

Unexamined Japanese patent application specification J 10-62371 (published Mar. 6, 1998) ("J 10-62371"

hereinafter) for "A process and apparatus for measuring boron, ultrapure water production apparatus and a process for the operation thereof" teaches measurement of boron in semiconductor-quality ultrapure water using boron-polyol complex chemistry. Polyol solution in J 10-62371 is deionized to remove ions that might otherwise contaminate the polyol with conductive ions. The process adds a low concentration of polyol to a sample stream and measures the conductivity of the resulting solution at least after such addition. In a first version (FIG. 1 of J 10-62371) polyol is pumped out of a storage container, through a pump, through a mixed bed ion exchange resin and into the sample stream. The reaction product is measured with a conductivity sensor. In a second variation (FIG. 2), the conductivity of the sample stream is measured before and after injection of deionized polyol solution. In a third version (FIG. 3), polyol is continuously recirculated through a pump, a mixed bed ion exchanger, and a polyol storage tank. On command from an electronic control unit, a second pump and valve are activated to remove deionized polyol from the recirculating loop and add it to the sample stream.

This approach also has some superficial similarities to the present invention in that the detector of J 10-62371 is intended for measurement of very low levels of boron as needed in the semiconductor industry, and polyol is deionized before it is added to the sample stream. There are a number of critical differences, however, between the apparatus and method taught by such application and the present invention.

First, although the detector of J 10-62371 is intended to measure low levels of boron in ultrapure water, the design and operation of the device do not lead to sensitive enough results for practical on-line analysis of very low boron levels due to multiple, critical deficiencies in the design and operation of such detector.

One such deficiency is that the injection of polyol in J 10-62371 is continuous and not a plug injection into a tube of small internal diameter (as in the present invention), and is therefore subject to changes in accuracy of boron measurements due to flow rate variations. A second deficiency is that J 10-62371 does not teach or suggest the critical importance of routinely correcting conductivity readings for conductivity of a polyol/boron-free sample. A third deficiency is that J 10-62371 does not teach or suggest the need for using concentrated polyol solutions to obtain the critically necessary sensitivity. Because of the foregoing deficiencies, the method and apparatus of J 10-62371 cannot successfully and accurately measure boron concentrations at the very low levels of the present invention.

Thus, in J 10-62371, the conductivity of a polyol/boron-free sample is neither routinely measured nor routinely used to correct the boron response of a polyol/boron-containing sample. Instead, the approach of J 10-62371 includes the steps of measuring the conductivity of a polyol-free sample containing boron, and then subtracting this polyol-free conductivity from the conductivity of a polyol/boron-containing sample as conductivity correction. Such conductivity correction may be easier to carry out, but, critically, it yields very different and less accurate results as compared with the conductivity correction procedure of the present invention. That is because the conductivity correction method of the present invention corrects for conductivity effects attributable to polyol/boron-free sample water solution, while the J 10-62371 method does not do so. Use of relatively much higher concentration polyol solutions, another feature of the present invention as discussed below, leads to even greater conductivity effects attributable to polyol/boron-free samples thereby further increasing the need for the conductivity correction method of this invention.

In the process of J 10-62371, concentrations of polyol after mixing with boron containing samples are so low they do not exert significant conductivity increases. The concentration of mannitol solution at the conductivity cell in J 10-62371 is reported as 0.0060 moles mannitol/l. At such concentration, conductivity background from a mannitol/boron-free sample (although not even suggested by J 10-62371) is not measurable. This fact explains why Table 1 in J 10-62371 shows the same resistivity (18.2 megaohm cm) before and after mannitol is added (18.2 megaohm cm). By contrast, with the present invention, the concentration of mannitol in the mannitol/boron-free sample is 0.32 moles/l. At this fifty times higher concentration of polyol, the conductivity background is 5.1 $\mu$S/cm higher than the conductivity of ultrapure water without polyol (0.055 $\mu$S/cm), and therefore must be accounted for, which is not taught or suggested by J 10-62371. In exchange for the higher polyol concentration of the present invention necessitating an additional corrective step, however, the conductivity response per ppb of boron of the present invention is greatly increased (by 8 times at 0.05 ppb boron to 14 times at 10 ppb boron) relative to the response obtained using the technique of J 10-62371.

The concentration of polyol solution is so low in J 10-62371 that it causes measurement of boron to not be very sensitive. Thus, in such application, polyol is added at a very dilute concentration to conserve polyol use. FIG. 13 of the present application shows the critical effect of using low concentrations of polyol on measurement of boron, comparing data for the device of J 10-62371 with comparable data using the apparatus and method of the present invention. It can be seen that the conductivity response curve for data resulting from the J 10-62371 device/process is relatively flat, making it critically difficult to determine very low concentrations of boron over the range 0–10 ppb. By contrast, the conductivity response curve for comparable data generated using the present invention is quite steep thereby clearly differentiating boron concentration differences of as little as 0.05 ppb based on critically significant changes in the conductivity. Achieving such critically greater sensitivity in conductivity measurements, however, has been found to require use of much more concentrated polyol solutions, which as discussed above is completely inconsistent with the design and operation of the device taught by J 10-62371.

J 10-62371 does not teach that the difference between conductivity of a polyol/boron-containing sample and conductivity of a polyol/boron-free sample is mathematically accurately correlated to a low-level concentration of boron in such sample over the range of very low levels of boron. J 10-62371 also does not teach that the concentration of the polyol solution must be relatively high (i.e., preferably greater than 0.05 M polyol/l) in order to obtain the critical high sensitivity response needed for accurate low-level boron measurements. J 10-62371 certainly does not teach the use of both of these techniques in combination.

Another distinction between J 10-62371 and the present invention is that the former does not teach or suggest injection of microliter volumes of high concentration polyol into a boron-containing sample. Furthermore such patent application teaches continuously injecting polyol into a continuously flowing sample stream, but this approach requires a large volume of polyol reagent. Additionally, the method of J 10-62371 is sensitive to any changes in the ratio of flow rate of polyol injection relative to sample flow rate.

By contrast, the present invention is not sensitive to changes in sample flow rate because in the preferred embodiment a small plug of polyol is inserted into the sample stream, and dilution is fixed by a combination of the laminar flow, surface tension and diffusion within the micro dimensions of the apparatus.

Still another critical difference is that the present invention uses just one pump and one valve both to recirculate polyol solution through the deionization resin bed and to insert a micro-plug of polyol into a tube containing the sample stream and having a small inside diameter. By comparison, FIG. 3 of J 10-62371 requires two pumps to achieve the same functions. Where J 10-62371 teaches use of only one pump (as shown in FIGS. 1 and 2 thereof), it does not include recirculation of polyol through a deionization resin bed. As shown in FIGS. 1 and 2 of said application, a pump pumps polyol from polyol storage compartment, through the pump, through a deionization module and then into a sample stream. As a result, the methods of FIGS. 1 and 2 of J 10-62371 require accurate flow measurements and controls, and use a large amount of polyol for each boron analysis.

The consumption of polyol is much less for the present invention than for the J 10-62371 because in the present invention polyol micro-pulses are injected into samples. By contrast, the Japanese application uses a continuously flowing stream of dilute polyol added to continuously flowing sample, even when polyol addition is only made periodically. By contrast, the present invention adds polyol accurately in micro-injections of only 25 $\mu$l or 50 $\mu$l. The apparatus of J 10-62371 requires large tanks to store the large volume of polyol required for such process. Typical flow rates of polyol and sample used in J 10-62371 are 1.44 /hr (24 ml/min.) and 15 l/hr (250 ml/min.) respectively. The mannitol has a concentration of 12.5 grams/liter or 12.5/182=0.069 moles/l. Therefore, the method of J 10-62371 uses 0.069 M/l×1.44 l/hr.=0.01 moles (18 grams) mannitol/hr. to measure boron in the sample. By comparison, the present invention uses only 50 $\mu$l of a 1.0 molar (182 g/l) mannitol solution or 5×10$^{-5}$ moles (0.009 grams) mannitol/injection. Based on a typical 12 injections per hour, the present invention uses 6×10$^{-4}$ moles (0.1 grams) mannitol per hour, only about $\frac{1}{180}^{th}$ the mannitol consumption of J 10-62371.

Another recent journal article entitled "Determination of Boron by Flow Injection Analysis Using a Conductivity Detector" by S. D. Kumar, et al.; *Analytical Chemistry*, Vol. 71, No. 13 (Jul. 1, 1999) pages 2551 to 2553, teaches use of an injection valve to inject a 100 $\mu$l volume of a boron containing sample into a stream containing 0.3 M mannitol flowing at 1 ml/minute. The combined streams are flowed into a mixing tube, and then into a 6 $\mu$l volume conductivity cell where conductivity change is measured. The linear boron measurement range of this method is reported as 0–20 ppm as B, and the lower limit of detection is reported as 10 ppb as B. When there are interfering ions in the sample, a pre-treatment procedure to remove them is employed. This pre-treatment procedure, however, requires stirring a strong base anion exchange resin in the Cl$^-$ form with an aliquot of the sample to convert all ionized anions to the Cl$^-$ form. After filtration, such pre-treated solution is passed through a column containing cation exchange resin in the Ag$^+$ form to remove all chloride and ionized cations. As Kumar et al. point out, the method does not remove weak acid anions such as acetate, formate and bicarbonate quantitatively.

Here again, the apparatus and method of Kumar et al. have some superficial similarities to the present invention in that both methods and apparatus use flow injection analysis to measure boron in solution, and the concentration of the mannitol solution is similar in both designs. Kumar et al. inject a boron-containing sample into a flowing mannitol solution whereas the present invention, critically, injects concentrated mannitol into a flowing sample stream.

There are numerous critical differences between the method and apparatus taught by Kumar et al. and the present invention. The dynamic range of the analyzer of the present invention is from 0–1000 ppb as B, whereas the device of Kumar et al. measures from 0–20 ppm as B. For the Kumar et al. device, the lower limit of detection (LOD) is 10 ppb as B. while the present invention has a LOD as low as 0.05 ppb as B (200 times lower). The response factor is also critically different between the two methods. The Kumar et al. response is 0.5 $\mu$S/ppm B. By contrast, the present invention shows a response factor of 17 $\mu$S/ppm B, a 34 times improvement.

Still another critical deficiency is that the Kumar et al. method of injecting a sample as a slug into a flowing 0.3 M mannitol stream is not efficient with respect to reagent consumption. If a measurement were made every 10 minutes, the amount of polyol consumed over 6 months would be 13,100 ml of 0.3 M mannitol (720 grams mannitol) calculated as (0.5 ml/measurement)×6 measurements/hr.×24 hr./day×182.5 days). In contrast to such method, the method of the present invention provides conversely and critically for the injection of polyol as a micro slug directly into a flowing sample stream (both for boron-containing water and for boron-free water). The invention of the present application requires an injection volume of 25 $\mu$L of polyol per measurement into the sample stream. The volume of 1 M mannitol used over the same six month period thus would be only 655 ml (120 grams mannitol). This amount is six times less mannitol than that required for the process of Kumar et al., and twenty times less solution. This extremely efficient use of polyol is very important and practical for on-line boron measurements as it makes possible the use of reagent containers of a reasonable size.

Kumar et al. do not teach deionization of concentrated mannitol solution. This step has been found to be critically important if low-level boron concentrations are to be measured accurately. Such failure by Kumar et al. probably explains their LOD of only 10 ppb as B.

The present invention uses a micro conductivity cell that is only one-third the volume of the Dionex conductivity cell used in the Kumar et al. device. Both cells have a cell constant of one. The smaller conductivity detector volume of the present invention improves the conductivity peak resolution, accuracy and sensitivity. Kumar et al. also do not teach the importance of thermal correction of conductivity measurements, nor do they teach the importance of demineralizing polyol.

Thus, there remains an unmet need in the art for an inexpensive boron detection and measurement system which can be made light-weight, compact and portable, and which is capable of accurately and reproducibly measuring extremely low concentrations of boron in water on-line. This need is met, and the aforementioned drawbacks and limitations of the prior art boron detectors are overcome, in whole or in part, with the low-level boron detection and measurement system of the present invention.

OBJECTS OF THE INVENTION

Accordingly, a principal object of this invention is to provide methods and apparatus for very low-level boron detection and measurement in aqueous solutions.

It is a general object of this invention to provide methods and apparatus for a boron measurement system for use in semiconductor manufacturing and other applications which require accurate, reliable measurement of boron at very low concentrations, e.g., 0.050 ppb B or less.

An additional object of this invention is to provide a boron measurement system for low-level measurements of boron in water utilizing highly concentrated polyol solutions in very small quantities.

Another object of this invention is to provide a boron measurement system for low-level measurements of boron in water utilizing accurate, small, periodic injections of high concentration polyol solution into a boron-containing aqueous sample to form an ionized complex resulting in a substantial, measurable increase in the electrical conductivity of the sample even at very low boron levels, e.g., 0.05 ppm as B or even less.

A further object of this invention is to provide a boron measurement system for low-level measurements of boron in water in which there is a mathematically correlated relationship between (a) the difference in electrical conductivity of a boron-containing sample which has been mixed with a polyol and the electrical conductivity of polyol/boron-free sample, and (b) the concentration of boron in the sample over a boron concentration range of less than 0.050 ppb B to about 1000 ppb B.

Yet additional objects of this invention are to provide a low-level boron measurement system which minimizes required amounts of polyol; corrects for conductivity effects of polyol/boron-free sample; and is not sensitive to variations in flow rates of boron-containing samples or polyol solution.

Other objects and advantages of the present invention will in part be obvious and will in part appear hereinafter. The invention accordingly comprises, but is not limited to, the methods and related apparatus, involving the several steps and the various components, and the relation and order of one or more such steps and components with respect to each of the others, as exemplified by the following description and the accompanying drawings. Various modifications of and variations on the method and apparatus as herein described will be apparent to those skilled in the art, and all such modifications and variations are considered within the scope of the invention.

SUMMARY OF THE INVENTION

This invention is generally directed to methods and apparatus for accurately measuring very low concentrations of boron in deionized water. It utilizes the chemical reaction of boric acid with a polyol, such as mannitol or other similar compounds, to produce an ionized acid product which can then be measured by a conductivity and temperature detector. Boric acid is only weakly ionized (pKa=9.23 at 25 C.) in pure water. The reaction of boric acid with a polyol, such as mannitol or sorbitol, however, forms a complex that is more strongly ionized (pKa=5.14 with mannitol) and causes a dramatic increase in electrical conductivity that can be measured at even very low levels of boron in water if interfering or extraneous factors which can affect conductivity are either eliminated or corrected for.

Surprisingly, it has now been found that one can accurately measure very low levels of boron in water by injecting very small plugs or aliquots of concentrated polyol into streams of boron containing and non-boron containing water samples, and then measuring the conductivity difference (delta conductivity) between such boron containing and non-boron containing samples. Critically, it has been determined that the actual boron concentration remains mathematically correlated to such delta conductivity measurement over the industrially important low-level range of boron concentrations. With these present new methods and apparatus, one can accurately measure concentrations of boron in water at very much lower boron levels than any prior art polyol conductometric measurement method. This new technique is as sensitive as the most sensitive conventional laboratory boron measurement methods (without pre-concentration), i.e., using inductively coupled plasma mass spectrometry (ICP-MS) or ion chromatography. The present invention, while just as sensitive as ICP-MS and chromatographic techniques, is vastly simpler, less expensive to purchase, and can be easily operated on-line by less skilled operators.

Another important aspect of this invention is the discovery that accurate measurement of a very low level of boron requires both thoroughly deionized polyol and a technique to account for the conductivity of the polyol reagent after it is added to boron-containing water. No prior art polyol-boron detection methods have ever recognized the importance of using thoroughly deionized polyol combined with the steps of measuring the conductivity of polyol/boron-free sample and correcting the polyol/boron-containing sample conductivity measurement to account for conductivity increases attributable to polyol per se in order accurately to determine very low-level boron concentrations in water. When polyol (at the concentrations needed for sensitive boron detection) is added to boron-free deionized water, the conductivity of that solution is greater than the conductivity of such deionized water. If such additional conductivity is not accounted for, an error is introduced in the final boron measurement. Simply passing concentrated polyol solution through an ion exchange resin before use is not sufficient to remove such inherent added conductivity. This is apparently because the polyol itself ionizes to a small extent. At very low levels of boron, failure to correct for this factor will lead to a very high percentage error.

In the present invention, polyol/boron-free sample conductivity is subtracted from polyol/boron-containing sample conductivity to obtain a "delta conductivity," and this delta conductivity is mathematically correlated to the true boron concentration of the boron-containing sample. The prior art does not combine deionized polyol with injecting concentrated deionized polyol into the flowing deionized (DI) water and with using "de-boronated" DI water to establish a base line. It is not obvious from the prior art that such combination enables precise boron analyses at the very low levels obtained with the apparatus and methods of the present invention.

DETAILED DESCRIPTION OF PREFERRED EMBODIMENTS

The present invention is directed to methods and apparatus for accurately measuring very low levels of boron in ultrapure water and having particular utility in manufacture of semiconductors. The present invention also overcomes limitations of prior art processes and devices thereby making possible rapid, inexpensive measurement of boron in ultrapure water at concentrations ranging from about 0.01 to 1000 ppb as boron with equipment which is relatively compact and inexpensive, and which can be run on-line by relatively unskilled operators.

Large amounts of ultrapure water are required in processes to manufacture semiconductors. Boron is a contaminate that must generally be removed to very low concentrations. As previously discussed, boron is a silicon semiconductor p-type dopant used in manufacture of silicon solid state electronics and functions as a principal charge carrier. Therefore, boron must not be added inadvertently during the manufacturing process. S. Malhotra et al. reported in their paper, "Correlation of Boron Breakthrough versus Resistivity and Dissolved Silica in a RO/DI System" (Ultrapure Water, 1996. 13(4): pp. 22–26) that boron was the first ion to breakthrough ion exchange resin beds when they switched to thin-film-composite (TFC) reverse osmosis membranes. The introduction of TFC reverse osmosis (RO) membranes to replace cellulose acetate RO membranes was very effective in reducing the silica passage (by a factor of 58) but less effective in reducing boron passage (by a factor of only 1.7).

The first ions to leak from mixed ion exchange resin beds which follow RO units are weakly ionized compounds such as dissolved silica and boron. With TFC RO membranes, silica passage is much less than boron passage. Boron is therefore often the first ion to breakthrough mixed ion exchange resin beds in water purification systems that use TFC RO membranes. This is especially true if the feedwater has high levels of boron in it. Adsorption of borate ion on anion exchange resins in the hydroxide form is the most common method to remove boron from ultrapure water. With usage, borate ion is one of the first ions to leak from the resin, rapidly reaching unacceptable levels.

Figure 12:
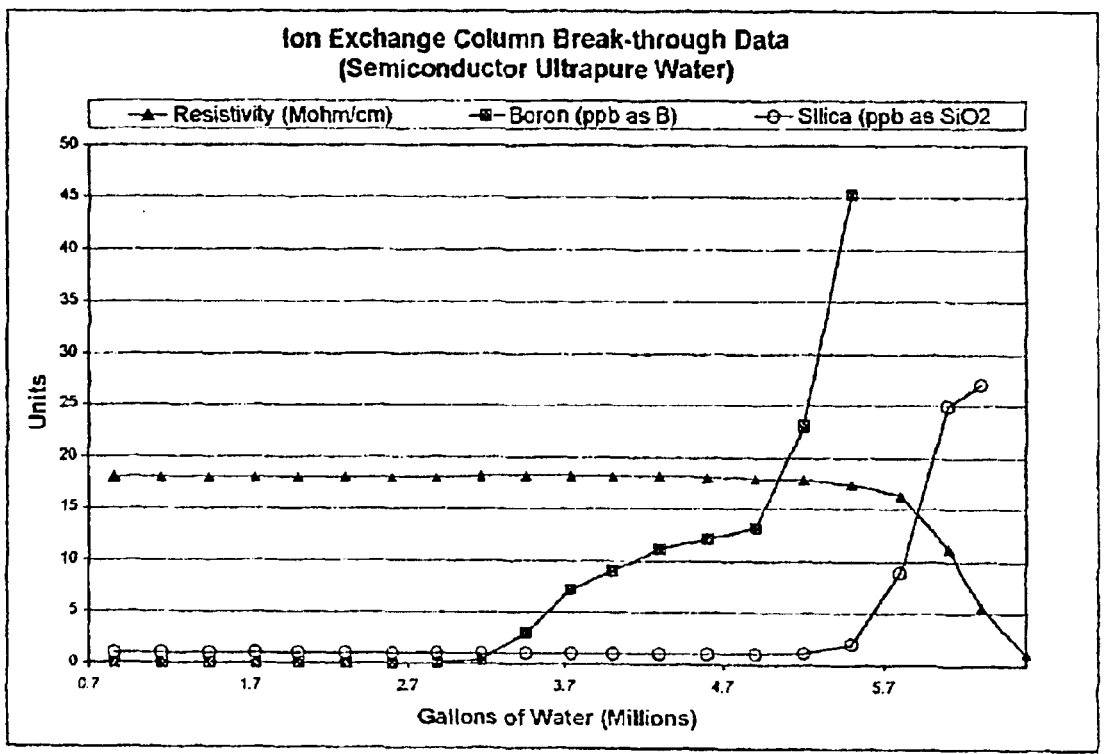
FIG. 12 is an illustrative graph showing ion exchange column break-through data, taken from prior art.
Figure 13:
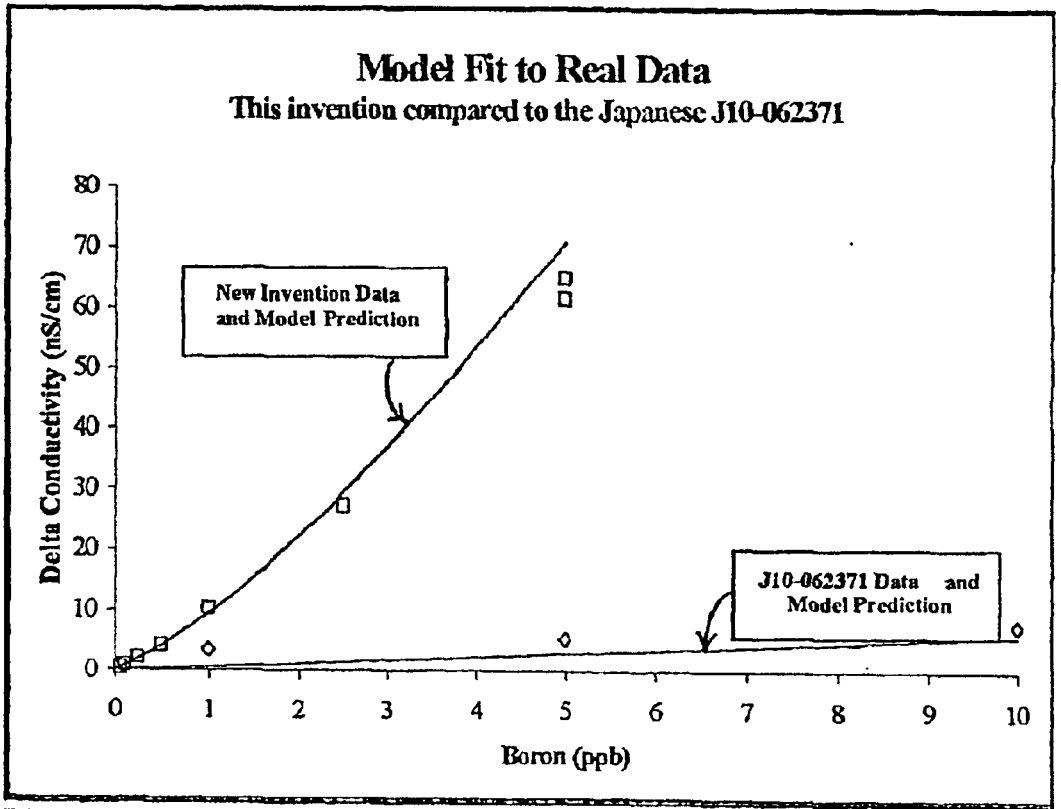
FIG. 13 is an illustrative graph comparing delta conductivity data generated utilizing a prior art process with delta conductivity data generated using the methods and apparatus of this invention.

FIG. 12 for example shows water resistivity, boron concentration, and silica concentration as a function of the amount of water passed through a mixed bed ion exchange column in a semiconductor factory as reported in the above-mentioned S. Malhotra et al. paper using TFC RO pretreatment. Typical concentrations of borate in ultrapure, semiconductor-grade water are 0.05 to 10 parts per billion as B. These levels can currently be measured with an ICP-MS (inductively coupled plasma and mass spectrometer) detector, but such equipment is very expensive, requires a skilled operator to achieve good results, and results can not be acquired very quickly. A typical acceptable upper allowable limit of boron concentration in water for silicon semiconductor manufacturing is from 0.1 ppb to 5 ppb. Because the breakthrough of B to unacceptable levels can happen quickly, an automated on-line detector is required to solve this need for frequent analysis on a real-time basis. Prior to the present invention, the problem of real-time, cost effective and accurate on-line process measurements of extremely low concentrations of boron in water had not been solved. The analyzer and methods of the present invention, however, are suitable for real-time, rapid, inexpensive on-line measurement of boron in ultrapure water used for example to manufacture semiconductor electronic circuitry.

In general, the method of the present invention comprises injecting a very small slug (less than 100 microliters) of a concentrated (greater than 0.1 molar) intrinsic polyol from time to time into a flowing stream of deionized water which it is desired to analyze for ortho-boric acid and/or the ionization products (anions) thereof. Such stream flows at about 100 microliters per minute. From time to time such stream, before intrinsic polyol injection, is diverted through a boric acid/borate selective (chelating) anion exchange resin to produce a stream substantially free of boric acid respectively borate but otherwise unchanged from the boric acid/borate-bearing stream. The electrical resistance (or electrical conductance) of the boron-bearing DI water stream, after injection of intrinsic polyol, is measured some distance downstream of the polyol injection point very frequently, e.g., 100 or more times per minute. The maximum value of the conductance found is taken to represent the combined conductance of polyol-boron complex and polyol not complexed with boron. The contribution to conductance from polyol not complexed with boron is obtained by injecting the same volume, same concentration of the same intrinsic polyol into the stream which has been substantially freed of boron, flowing at the same rate and measuring the representative conductance in the same manner as above. The so-obtained conductance of the polyol-boron-free stream is subtracted from the conductance of the polyol-boron-bearing stream giving a corrected conductance representing therefore only the conductance contributed by the polyol boron complex. Such corrected conductance is found to be uniquely and precisely and quantitatively related to the true borate content of the DI water analyzed, down to levels approaching 0.001 parts boron (as boron) per billion parts water, i.e., down to 0.001 micrograms boron (as boron) per liter of DI water.

As used above "intrinsic polyol" means polyol which is substantially free of all ions other than those due to the intrinsic ionization of the polyol per se. In this context, "substantially free of all other ions" means that the measured conductivity of the polyol is that solely of the polyol expressed to whatever significant figures are required for precise boron analysis at the boron concentration measured. Intrinsic polyol may generally be obtained by passing a solution of such polyol through a mixed bed of thoroughly regenerated strong acid cation exchanger, strong base anion exchanger and borate selective anion exchanger.

Similarly, with respect to the DI water stream being analyzed "substantially free of boric acid respectively borate" is a relative term meaning that after boron removal the resulting stream must have a borate/boric acid content much less than the DI water stream, e.g., $\frac{1}{10}^{th}$ as much. Thus, if it is desired to determine 0.001 ppb of B in the DI water stream, then the same stream relatively free of B should have no more than about 0.0001 ppb boron.

To obtain precise analyses of very low levels of boron, it is necessary to correct for the intrinsic dissociation/ionization of the polyol. In other words, such dissociation/ionization should be negligible at the boron levels to be detected and at the concentrations of polyol used. Other polyols may be superior to mannitol in this respect. In accordance with the teaching of this invention, such intrinsic dissociation/ionization of any polyol may be easily determined by anyone of ordinary skill in the art, e.g., by passing a solution of the polyol through the mixed bed ion exchanger (16 of FIG. 1), injecting the latter into DI water which has passed through column 3, and measuring the resulting peak conductivity.

This invention will be better understood by reference to FIGS. 1–13 which are discussed in more detail below.

Figure 1:
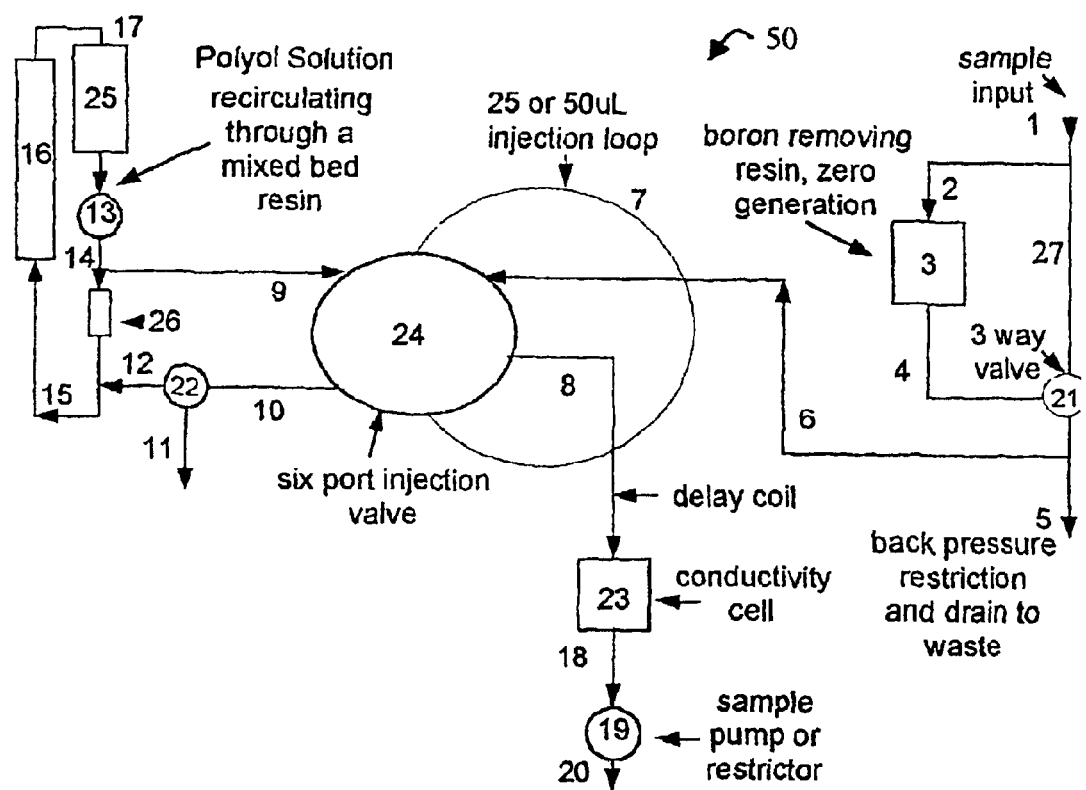
FIG. 1 is a simplified process flow diagram of one preferred embodiment of the present invention.

FIG. 1 is a schematic process flow diagram of one typical preferred embodiment of this invention. As seen in FIG. 1, a deionized but boron-containing water sample flows into boron measurement system 50 through conduit 1. To generate a boron-free water sample, 3-way valve 21 is initially positioned and adjusted to divert sample flow from conduit 1 into conduit 2, through a boron removal, preferably boron specific, resin column 3, then into conduit 4, through 3-way valve 21 into conduit 5, which includes a back pressure restriction (not shown), and finally to waste. Column 3 preferably contains a special boron-removal material such as Amberlite IRA-743T, manufactured by Rhom and Haas Company, Philadelphia, Pa., U.S.A. and (optionally but less preferably) a nixed strong acid and strong base ion exchange resin. A portion of boron-free sample is withdrawn from conduit 5 into conduit 6. This can be done either by action of downstream sample pump 19 or by means of an appropriately sized restrictor (instead of pump 19) which operates in conjunction with a pressurized feed into conduit 1 to control fluid flow rate. Withdrawn boron-free sample in conduit 6 is passed through a multi-port valve device or valve system, which as shown in FIG. 1 may advantageously comprise a six-port injection valve 24, and then passed out to conduit 8, which may be a delay coil, and then into conductivity and temperature measuring cell 23. A boron-free sample leaving cell 23 continues into conduit 18, through pump or restrictor 19, and then passes to waste through conduit 20. In place of six-port injection valve 24, one may substitute any combination of valves to achieve the same functions as six-port injection valve 24, as described hereinafter.

At the same time in the other portion of system 50, a polyol solution is recirculated through mixed strong acid and strong base ion exchange resin bed 16 to keep the polyol free of contaminating ions. Resin column 16 may optionally also include a boron removal resin such as Amberlite IRA-743T resin manufactured by Rohm and Haas Company or other equivalent boron-absorbing material. Polyol solution is stored in reservoir 25 from where it flows into pump 13, through conduit 14, into restrictor 26, through conduit 15, into resin column 16, and through conduit 17 back into reservoir 25. Between pump 13 and restrictor 26 along conduit 14, a portion of thoroughly deionized polyol solution is withdrawn through conduit 9 and is pushed by fluid pressure into six-port injection valve 24. Valve 24 is initially set in a first valve position which causes polyol solution to be pushed through injection loop 7, back into valve 24, and out through conduit 10 to a second 3-way valve 22, then through conduit 12, and back into the recirculating polyol stream along conduit 15. Fluid pressure is higher in conduit 14 than in conduit 15 due to restrictor 26 inline between them. This first position of six-port injection valve 24 allows the withdrawn portion of polyol to circulate through injection loop 7. Injection valve 24 is then actuated for changing the first valve setting to a second valve position, or is otherwise reset, so as to change fluid flow through the valve device. Flow of polyol solution now enters valve 24 through conduit 9, passes through valve 24 and exits valve 24 directly to conduit 10, no longer passing through injection loop 7. The portion of boron-free sample water in conduit 6 now enters valve 24 and flows through injection loop 7. This pushes polyol portion that was in injection loop 7 into conduit (or delay coil) 8 and from there into conductivity and temperature measuring cell 23, through conduit 18, through pump or restrictor 19, and then to waste through conduit 20. Electrical conductivity of boron-free sample-polyol mixture (herein the "polyol/boron-free sample") is measured in conductivity and temperature measuring cell 23.

Injection valve 24 is then actuated, or is otherwise reset, for switching back to the first valve position. Polyol solution now enters injection loop 7 and pushes out the boron-free sample water portion that was previously flowing through it. Such polyol solution next flows into conduit 10. A 3-way diverter valve 22 is actuated or set to divert the boron-free sample to waste. When the boron-free sample is expelled, 3-way diverter valve 22 is deactuated or reset so that effectively thoroughly deionized polyol once again circulates through the injection loop 7 and then back to the polyol deionization recirculation loop. This embodiment prevents the small amount of boron-free sample from mixing with and diluting polyol solution in the recirculation loop thereby preventing dilution of polyol over time.

To measure a boron-containing deionized water sample using boron measurement system 50 of FIG. 1, 3-way valve 21 in the sample inlet path is repositioned such that sample flow bypasses boron removal column 3. A boron-containing aqueous sample flows from sample inlet 1, through conduit 27 and valve 21, into conduit 5 with a portion flowing into conduit 6. Such boron-containing sample portion flows from conduit 6 through six-port injection valve 24, out to conduit 8, into conductivity and temperature measuring cell 23, out through conduit 18, through pump or restrictor 19, and then to waste through conduit 20. The polyol deionization loop during such mode is circulating polyol through injection loop 7 by conduit 9, into injection valve 24, through injection loop 7, back to injection valve 24, through conduit 10, through 3-way diverter valve 22 to conduit 12, and then back into the deionized polyol circulation loop. Injection valve 24 is then actuated or reset for changing the first valve setting to a second valve position so as to change fluid flow through the valve. The boron-containing sample water portion in conduit 6 now enters injection valve 24, goes into injection loop 7, thereby pushing the plug of polyol solution previously in injection loop 7 out of injection loop 7 and into conduit 8, through conductivity and temperature measuring cell 23, through conduit 18, through sample pump or restrictor 19, and out conduit 20 to waste. As the boron-containing sample and polyol mixture (herein the "polyol/boron-containing sample") passes through conductivity and temperature detector 23, the electrical conductivity and temperature of the polyol/boron-containing sample is measured.

Six-port injection valve 24 is then returned to the first valve position. This causes the boron-containing sample in conduit 6 to enter injector valve 24, pass directly through it and exit into conduit 8, through cell 23, conduit 18, pump/restrictor 19 and conduit 20 to waste. The deionized polyol solution in conduit 9 enters injector valve 24, passes through it and through injection loop 7, back into injector valve 24, out of valve 24 and through conduit 10. The boron-containing sample that was in injection loop 7 is now diverted to waste through conduit 11 from valve 22. When polyol again enters diverter valve 22, this valve is deactivated or reset so that polyol flows from conduit 10, through diverter valve 22, through conduit 12, and back into the recirculating deionized polyol loop through conduit 12. Once again, this process design prevents the boron-containing sample from mixing into the polyol loop thereby contaminating and diluting it.

The present invention lends itself to an even more simplified design based on a slight modification of the apparatus and method described above for FIG. 1. Such simplified design eliminates diverter valve 22. Such an apparatus modification can be effected by the additional modification of using a saturated solution of polyol (e.g., one gram-mole, 182 grams mannitol in 1000 ml water) in the recirculation deionization loop. For this slightly modified embodiment, excess solid polyol is maintained within polyol storage chamber 25. During operation of boron measurement system 50, the small amounts of aqueous samples (both boron-containing and boron-free) remaining in injection loop 7 after the polyol solution has been injected into the conductivity cell are added back and mixed into the polyol deionization recirculation loop. Small amounts of boron contained in the boron-containing aqueous sample portions of course, complex with the polyol, but the boron is then removed by equilibration with special boron-removing resin as part of the ion exchange resin packed in column 16 as previously described. As long as storage chamber 25 is maintained as the coolest component in the system (polyol recirculation, boron/polyol complex removal, and deionization loop), polyol will not precipitate out in small orifices of boron measurement system 50.

As previously discussed, a key aspect of the present invention is the method to account for the conductivity of the polyol/boron-free sample water solution. No prior art practitioners of polyol-boron detection methods have taught the importance of using concentrated, thoroughly deionized polyol combined with measuring the conductivity of polyol/boron-free sample and subtracting such background conductivity from the polyol/boron-containing sample conductivity measurement accurately to determine very low-level boron concentrations in water. In the present invention, polyol/boron-free sample conductivity is subtracted from the polyol/boron-containing sample conductivity, and this conductivity differential (delta conductivity) is mathematically correlated with true boron concentration of the boron-containing sample. When polyol at the higher polyol concentration range which we have found is critically needed for sensitive detection (preferably at least 0.05 M polyol, more preferably at least 0.1 M polyol, most preferably at least 0.3 M polyol) is added to boron-free water, conductivity of the resulting solution is significantly greater than the conductivity of deionized water. If this additional conductivity is not accounted for, an error is introduced in final boron measurement. Passing concentrated polyol solution through an ion exchange resin before mixing it with a sample is necessary but not sufficient to remove any additional conductivity effect. This is apparently due to the fact that polyol itself ionizes to a small extent. At low levels of boron, without correcting for this factor the error will be very high.

For example, at 25° C. mannitol has a pKa of 13.8, and a 0.32 molar solution exerts a conductivity cell of 0.0601 $\mu$S/cm, a delta conductivity increase of 0.0051 $\mu$S/cm over that of deionized water (0.0550 $\mu$S/cm). In measuring very low concentrations of boron in ultra pure water, polyol/boron-free background conductivity represents a substantial fraction of a measured conductivity signal for a polyol/boron-containing sample. When using 0.32M mannitol for measuring boron in water at a concentration level of 5 ppb, boron-free mannitol-water solution conductivity thus accounts for about eight percent of the conductivity signal for such mannitol/boron-containing sample. At 0.5 ppb B, background conductivity of a mannitol/boron-free sample represents over half of the conductivity signal for a mannitol/boron-containing sample. At 0.05 ppb B, conductivity background of a mannitol/boron-free sample accounts for about 93% of the conductivity signal for a mannitol/boron-containing sample.

Accurate conductivity measurements for a mixture of polyol and boron-free water must therefore be subtracted from conductivity measurements of a mixture of polyol and boron-containing water to determine accurate low levels of boron in ultrapure water. More precisely, the conductivity difference (delta conductivity) between a polyol/boron-containing sample and a polyol/boron-free sample has been found to be mathematically correlated to the true boron concentration in such boron-containing sample. An important aspect of this invention is the discovery that there exists such a mathematical correlation between true boron concentration and delta conductivity over the range of boron concentrations here of interest, namely from about 0.01 to 1000 ppb as boron, more particularly over the range of about 0.01 to 10 ppb as boron, as illustrated in FIGS. 2 and 3.

Figure 2:
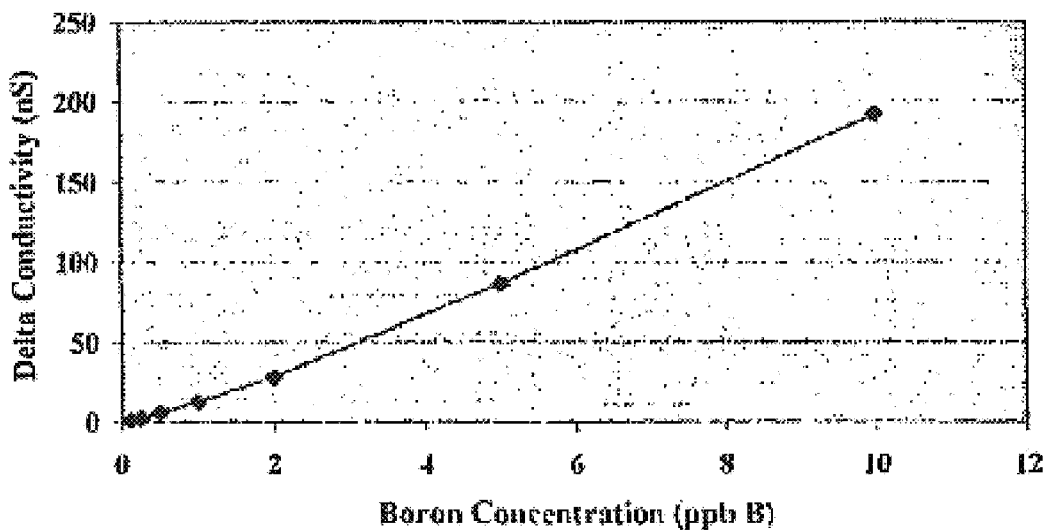
FIG. 2 is an illustrative plot of delta conductivity data versus boron concentration over the range of about 0–10 ppb as boron.
Figure 3:
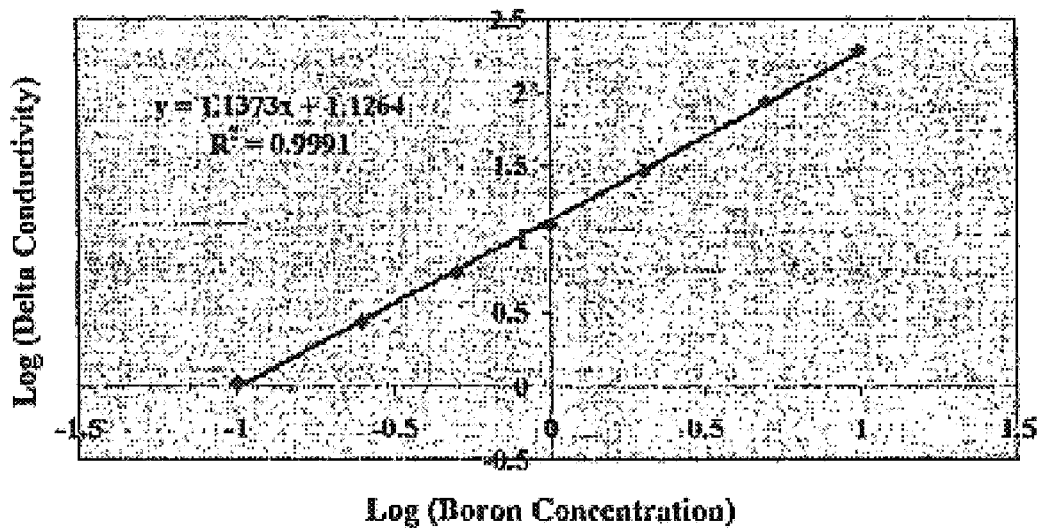
FIG. 3 is an illustrative log-log plot of delta conductivity data versus boron concentration.

FIG. 2 shows the result of measuring boron from 0.1 ppb B to 10 ppb B. The vertical axis shows the delta conductivity signal after polyol/boron-free sample conductivity is subtracted from the conductivity of polyol/boron-containing samples, the delta conductivity being reported in nano-Siemens per cm. This response is slightly curved, which is explained by a chemometric analysis of the reactions in terms of conductivity. The equations describing the chemistry underlying this analysis are discussed below. A log-log plot of the same data as shown in FIG. 2 is presented in FIG. 3. In FIG. 3, the slope of the line is 1.1373, the intercept is 1.1264, and it is substantially straight as determined by the Coefficient-of-Determination ($R^2$) value of 0.9991, illustrating that the delta conductivity data can be substantially linearized mathematically.

Figure 4:
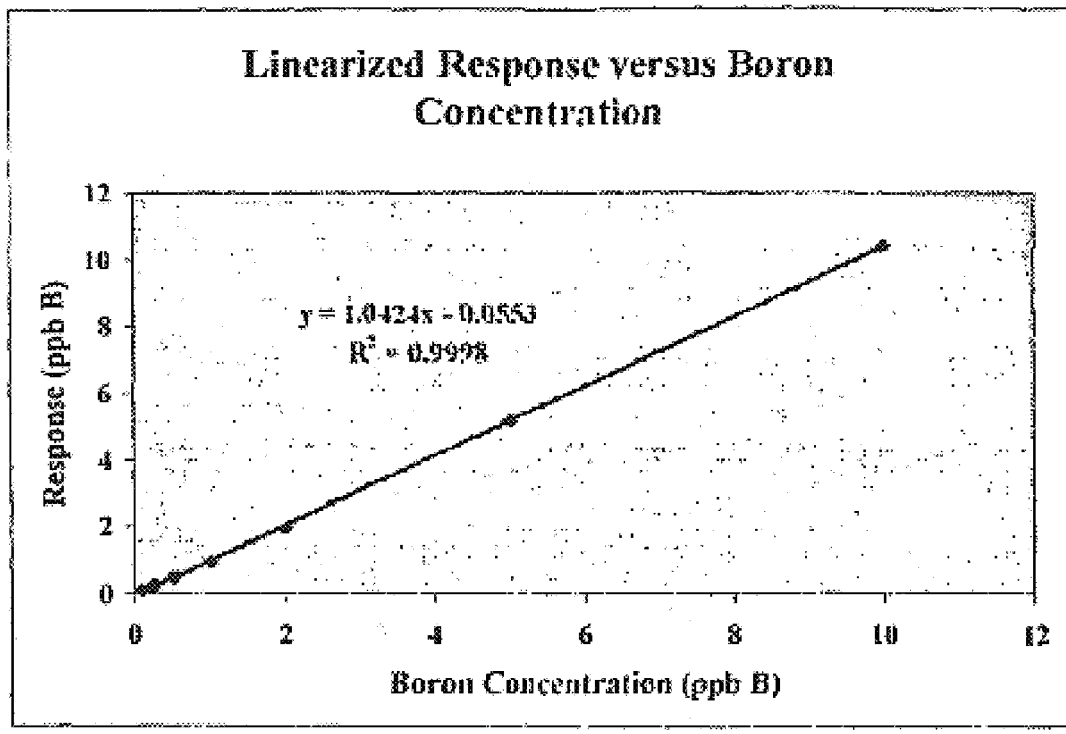
FIG. 4 is an illustrative graph of linearized response data versus boron concentration.
Figure 5:
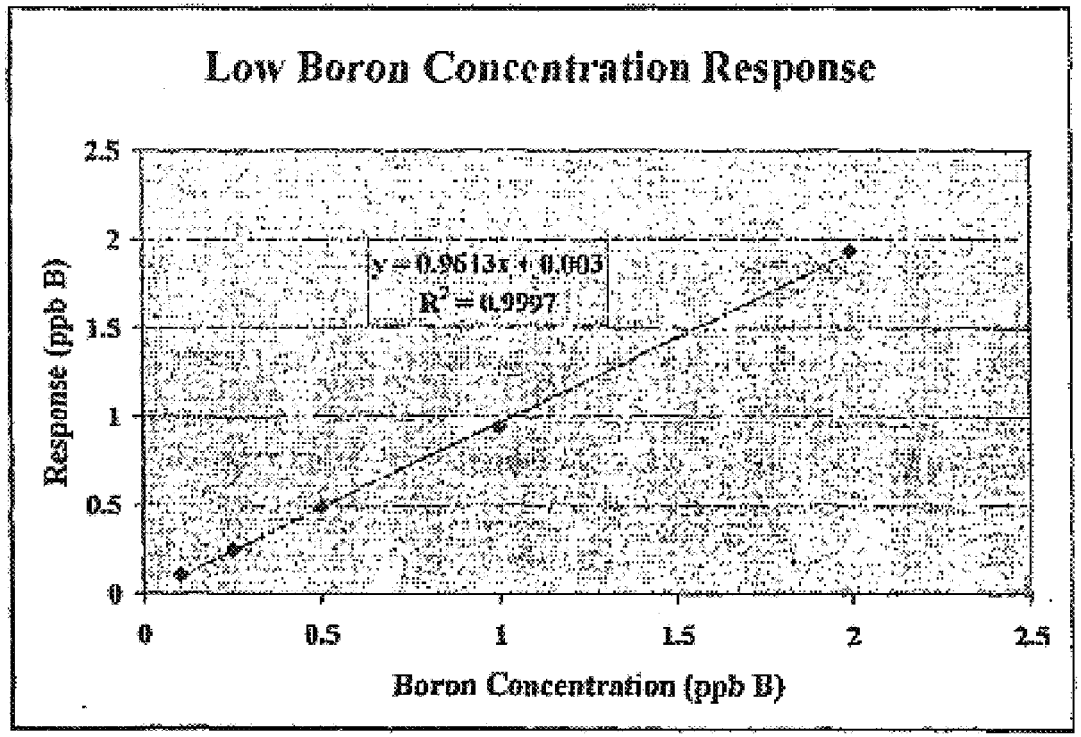
FIG. 5 is an illustrative graph of concentration response versus boron concentration at very low boron concentrations of about 0–2.5 ppb as boron.

A transform equation can be derived empirically or analytically from the reaction equations. The empirically determined transform is shown in FIG. 4 and is based on Log(Delta Cond.)=1.1373 Log(Boron Conc.)+1.1264 or Boron Conc.=0.10223 (Delta Cond.)$^{(0.8792)}$. This transform of the experimental delta conductivity data values produces a straight line of measured B concentration vs. true B concentration with a slope of 1 and an intercept of zero, as seen in FIG. 4. The same transform of the same delta conductivity data from the same boron analyzer is shown in FIG. 5 for four lower boron standard concentrations. FIG. 5 shows very good linearity and accuracy even at very low concentrations of boron.

Another novel feature of the present invention is the apparatus and method for providing a reference stream of water with essentially zero level of boron. Such boron-free sample is required to be introduced from time to time into the boron detector system of this invention for measurement of background conductivity of thoroughly deionized polyol/ boron-free water in order to achieve accurate low level results in accordance with this invention. Water having zero level of boron can be generated by the use of special boron removing resins having boron-attracting functional groups. Rohm and Haas Company manufactures one such resin, Amberlite IRA-743T. This resin has a polyol (glucamine) functional group attached to a cross-linked polystyrene support matrix. The improved boron removal efficacy of this special resin over a conventional strong base resin is reported in "Application of Boron Selective Resin in an Ultrapure Water System", M. Tanabe and S. Kaneko, published in the proceedings of the 1996 Semiconductor Pure Water and Chemicals Conference at pages 98–107 and in U.S. Pat. No. 5,833,846, which is incorporated herein by reference.

Still another important aspect of the present invention is the ease with which it can be adapted for on-line use. The design of apparatus which adds effectively deionized polyol to a sample must have specific characteristics to achieve accurate low level boron measurements and to allow characteristics suitable for on-line process analysis. Practical, inexpensive and low maintenance on-line process analyzers benefit greatly from simple design, reliable operation, simple service and maintenance requirements, low reagent consumption, small sample requirements and absence of need for skilled operators. In the present invention, changes in sample conductivity when measured at low boron concentrations are of the order of 0.5% of the conductivity of deionized water. Accurately to measure such low conductivity changes requires highly reproducible additions of essentially deionized polyol. One embodiment which is well suited for this invention is to use a six-port valve as part of a reagent loop injection device, as described above in connection with FIG. 1. Careful design of the reagent loop and a downstream delay coil geometry in accordance with this invention are used to control intermixing of polyol with a water sample for maximum reproducibility of results and signal-to-noise response. The injection of a polyol plug into a water sample has been found to create mixing conditions for polyol and sample which automatically achieve maximum reproducibility of results and also make this measurement method substantially insensitive to sample flow rate. This effect is due to laminar flow profiles, surface tension, and diffusion effects which result in mixing that is substantially not a function of reagent and sample flow rates.

Another advantage of such loop injection technique is that sample flow rate is not a sensitive parameter, Table 1 below illustrates the very low sensitivity of boron response (based on delta conductivity peaks), using the injection technique of this invention, to changes in sample flow rate.

TABLE 1

20 ppb Boron Injection with 0.097 $\mu$S/cm
(10.3 Megaohm cm)
Boron Free Water Blank

| Sample Flow Rate ($\mu$l/min.) | Delta Peak Height (Conductivity - $\mu$S/cm) |
|---|---|
| 225 | 0.31 |
| 450 | 0.30 |
| 900 | 0.28 |

It is known in the art (e.g., Shaefer et al. Z analyt. Chem. 121 (1941) p. 170) that iron and aluminum interfere with the determination of $B(OH)_3$ by titration of cis-1,2-diol adducts. Boron, iron and aluminum are all electron deficient atoms useful as catalysts in electrophilic reactions. Iron and aluminum may also interfere with the determination of boron according to the method of this invention. It is possible that the following elements may interfere with such determination:

A. Possibly very interfering: $Al^{+3}$, $Ga^{+2}$, $Zr^{+4}$, $Hf^{+4}$, $Sb^{+5}$, $Nb^{+5}$, $Ta^{+5}$, $Mo^{+6}$, $Mo^{+5}$ ($Ga^{+3}$ and/or $Ga^{+2}$ could be present in interfering amounts in recycled ultrapure water from a GaAs semi-conductor facility).

B. Possibly moderately interfering: $In^{+3}$, $Sb^{+5}$, $W^{+6}$, $Re^{+5}$, $Fe^{+3}$, $Zn^{+2}$, complexes of $Al^{+3}$, $Ga^{+3}$ or $Sb^{+5}$ with organic nitrocompounds.

C. Possibly competing with $B(OH)_3$ on an equal basis: $Sn^{+4}$, $Ti^{+4}$, $Re^{+3}$, $Fe^{+2}$, $Pt^{+4}$.

If the method and apparatus of the present invention give results at very low levels of boron in any given water which are in conflict with other methods and apparatus (e.g., Inductively Coupled Plasma Atomic Emission Spectrometry, or Inductively Coupled Plasma Mass Spectrometry), then it may be worthwhile to suspect the presence of one or more of the above electron-deficient cations and search for such.

Alternatively, in another embodiment of the present invention, non-ionized boric acid (i.e., in an essentially neutral solution) is allowed to diffuse across a membrane into a large excess of effective polyol. Such membrane should be substantially permeable to non-ionized boric acid and substantially impermeable to polyol, to ions and to colloids. Examples of such membranes include, without limitation, Reverse Osmosis and Nanofiltration Membranes and Perfluoro Sulfonic Acid Membranes. The driving force for diffusion of non-ionized boric acid is an activity gradient of boric acid per se. If the latter is highly complexed on the polyol side of such membrane, then "free" boric acid on such side can be very low. An increase in conductivity on such polyol side is representative of the (much lower total) concentration of boric acid on the "pure" water side of such membrane. Such polyol should itself contribute only a trivial (but known) amount of conductivity.

If a micro-conductivity-temperature measuring cell is used, then the membrane-diffusion cell can also be micro, e.g., the thickness of each chamber (i.e., the polyol chamber and the sample water chamber) can each be 1 millimeter or less to facilitate diffusion within the chambers. The chambers may contain structure to support the membrane and/or to promote mixing of the contents of either or both chambers. The membrane diffusion cell may comprise hollow fiber, hollow fine fiber or "spaghetti" membranes or a bundle of such microtubes arranged within one or more larger tubes. The polyol solution may be in the lumen of such microtube or tubes and the sample solution external to the latter. Alternatively, the sample solution may flow through such lumen in which case the polyol solution is external to the microtube or tubes. Preferably the polyol chamber is operated on a pulsed (stop-flow) basis and the boric acid side on a continuous flow basis. The polyol will then approach (but theoretically never reach) equilibrium with the inlet concentration of boric acid on the sample water side of the membrane. Periodically (after the polyol has reached a reproducible fraction of approach to equilibrium, e.g., 95% or 98%), the boron-laden polyol can be pulsed through such micro-conductivity temperature cell which can be read as described elsewhere herein.

The boron-laden polyol can be recycled/reused by passing it, after conductivity-temperature measurement, through a mixed bed of strong acid cation exchange resin and strong base anion exchange resin and a bed of boron specific ion exchange resin to produce essentially intrinsic polyol. Alternatively such mixed bed and such boron specific resin may be mixed together.

If such polyol is inexpensive, biodegradable and non-toxic, it may be sent to waste after conductivity-temperature measurement. An advantage of such membrane-diffusion system however is that polyol may be recycled/reused, permitting use of expensive but very effective polyols, e.g., cyclohexanehexone hydrate.

It has been pointed out herein that it is essential to determine the conductivity of boron-free polyol solution in order to make sensitive determinations of low level boron. Such is readily accomplished with the above-described membrane-diffusion cell. Conductivity and temperature of intrinsic polyol solution may be measured before or as such solution enters such membrane-diffusion cell or preferably by the same conductivity-temperature micro-cell used to measure boron-laden polyol. In the latter case, when boron-laden polyol is forced out of the membrane-diffusion cell by intrinsic polyol solution, the highest conductivity measured corresponds to boron-laden polyol and the lowest conductivity to intrinsic polyol solution.

Alternatively, instead of pulsed polyol solution in one chamber of the membrane-diffusion micro-cell, the polyol chamber may be operated continuously, countercurrent to the boron containing water stream. The polyol solution may flow at a slower rate, even a much slower rate, than the opposing water stream. Whether pulsed or continuous, the two chambers of the membrane-diffusion cell may be linear or structured, e.g., in spiral or tortuous path form.

The apparatus of FIG. 1 may be readily modified to include such a membrane-diffusion micro-cell. Boron-removing resin bed 3 and three-way valve 21 may, if desired, be retained as an additional check on the meaning and/or accuracy of any boron determination. Boron removing bed 3, generally containing only boron specific resin, removes only boron and little, if any, other electrolytes including ions which may interfere with a polyol-boric acid determination. As pointed out above, a membrane-diffusion cell should eliminate any such interference as well as having other advantages.

In addition to diffusion of non-ionized boric acid through the membrane of the above-described membrane-diffusion micro-cell, water will also diffuse through the membrane in response to any osmotic pressure difference generated by polyol solution. For example, a 1 molar solution of mannitol or sorbitol has an osmotic pressure of about 25 atmospheres. If the pulsing of the polyol solution is carried out on a controlled time basis, then the amount of water diffused and any dilution of the polyol will be reproducible. Alternatively, in such stopped flow mode, flow may be stopped by valves at each end of the polyol chamber of the membrane-diffusion cell (e.g., by solenoid valves) in which case the transmembrane pressure will rapidly build up to the osmotic pressure, and water flow (but not boric acid flow) will cease across the membrane.

As discussed herein, the purpose of boron removing resin 3 in FIG. 1 hereof is typically to remove solely boron, but no other electrolytes, to provide a boron-free water sample to be used for correction of the conductivity of a boron-bearing water sample. On the other hand, the latter may have a concentration of non-boron electrolytes sufficient to interfere with the accurate determination of very low levels of boron and/or, as also discussed herein, may contain interfering ions. In either case, it is preferred (according to another embodiment of this invention) to remove at least partially all electrolytes except boric acid and its anions at sample inlet 1 of FIG. 1. It is now disclosed, according to this embodiment, that a boron-bearing but substantially interference-free sample stream can be prepared by passing such sample stream through a mixed bed resin consisting of a strong acid cation exchanger and an anion exchanger which does not absorb boric acid but does absorb free acids stronger than boric acid. Amberlite IRA68 (Rohm and Haas Company, Philadelphia, Pa., U.S.A.) based on N-(acrylamidopropyl)-N,N-dimethyl amine is an example of such an exchanger. It is said to be the most basic of the so-called weakly basic anion exchange resins, sufficiently basic to form a salt with $CO_2$ (carbonic acid) but not with $SiO_2$ (silicic acid) and therefore also not with boric acid. One of ordinary skill in the art can readily test other anion exchange resins by means well known in the art for many years to determine if they have the property of not substantially absorbing dilute boric acid but substantially absorbing acids stronger than boric acid. Amberlite IRA68 is a gel-type anion exchanger. There may be an advantage to using a macroporous (sometimes called macro-reticular) equivalent of IRA68 to improve the removal of trace interfering colloids. Similarly it may be advantageous to use a macroporous strong acid cation exchanger in such pretreatment bed.

Following such pretreatment according to this aspect of the invention, the effluent of such pretreatment is preferable divided into two fractions, one passing directly to the polyol-boron measuring unit per se and the second fraction through boron removing means 3 of FIG. 1.

The cation exchange resin of the above described pretreatment system (for removing electrolytes stronger than boric acid), may also include cation chelating cation exchange resins, cation exchange resins containing phosphoric or phosphinic acid groups or even carboxylic acid groups.

The apparatus and method of this invention may advantageously incorporate a device and method alternatively to supply a standard, calibration and/or test sample of boric acid of known, very low concentration. Suitable devices and methods are described in U.S. Pat. Nos. 5,837,203 and 5,976,468, which by reference thereto are incorporated in their entireties into the present invention. In essence such applications pertain to analysis apparatus for analyzing fluid flowing between an inlet and a drain, the apparatus comprising:

(a) an assembly adjacent to a fluid region defined in part by such assembly, the assembly including an input port fluidically coupled to the fluid inlet, to the fluid region and to an output port, the output port defined by a first conduit having a hollow interior, an inlet end in the fluid region and an outlet end external to the fluid region and (b) an analyzer linked in-line with the fluid stream, the analyzer including an analyzer inlet fluidically coupled to the outlet end of the first conduit, whereby an analysis fluid flow path is defined from the fluid inlet seriatim through such inlet port, such fluid region and such inlet end of such first conduit, such hollow interior of the latter, such outlet end of such first conduit, such analyzer inlet and such analyzer.

The above mentioned assembly and related components must of course be made of materials which do not sorb boric acid or its anions, contribute boric acid or its anions or otherwise change the electrolyte concentration of the water being analyzed for boron. Polyvinylidene fluoride and polypropylene appear to be suitable materials. Glass appears not to be suitable.

By comparison, prior art continuous blending or mixing methods for conductometric polyol based boron detectors are relatively sensitive to variations in flow rates of either polyol reactant or boron-containing water sample stream. Standard flowmeters and metering valves are typically used to proportion the two flows. Because it is difficult and expensive to control very small flow rates of reagent and sample, such other methods require large amounts of polyol reagent. Compared to the polyol injection method of the present invention, the amounts of polyol needed for blended stream flows are greater and negatively affect the viability of on-line boron measurement. By contrast, the reagent loop injection method incorporated into this invention, as previously described, requires only very small volumes of polyol reagent, typically on the order of less than 25–50 microliters per injection. Such small polyol volumes make it possible, indeed necessary, to use a correspondingly small injector valve, sample tubing having a small inside diameter, small mixing tee, small delay coil, and a micro-conductivity and temperature sensor to achieve good detection sensitivity.

The conductivity cell used in the present invention must be very small to achieve conductivity peak resolution sufficient enough accurately to detect a peak response and to minimize reagent consumption. The volume of the conductivity cell sample chamber used in generating data for the present invention is for example 2 microliters, and the inside diameter of the conductivity cell flow path is 0.5 mm. The cell constant is 1.0 cm$^{-1}$.

The electronics used in this invention must very accurately determine small changes in conductivity. For example, to achieve a lower limit of detection of 0.05 ppm boron (based on three times the standard deviation of measurement), the electronics and the conductivity sensor must have a minimum standard deviation of about ±0.03 nS/cm. This level of precision can be achieved for example by using bipolar pulse conductivity measurement methods. A reference describing this type of conductivity measurement is Geiger, R. F., *Microcomputer-Controlled Instrumentation for Analytical Conductance Measurements using the Bipolar-Pulse Technique* (Doctoral Thesis University of Illinois at Urbana-Champaign, 1983), which publication is incorporated herein by reference.

As discussed above, construction of a commercially practical on-line boron analyzer which is sensitive enough to be of practical use to monitor ultrapure water for use in the semiconductor industry requires a low-volume conductivity cell, very sensitive and very stable electronics, a micro-volume polyol injection device, and a method to correct conductivity data as a function of temperature. Such a boron analyzer in accordance with this invention is small and designed so as not to consume large amounts of reagent. A boron analyzer of this design uses, for example, 330 ml of polyol reagent over a three month period of on-line operation. Such amount of reagent is easily contained as part of the analyzer. This feature of the invention is in sharp contrast to the large amounts of reagent required for prior art boron analyzers.

Another novel aspect of the present invention involves recirculating polyol through a deionization resin to remove residual conductivity from all other ionic sources such as carbon dioxide and bicarbonate. Tests using a mixed strong acid and strong base ion exchange resin in column 16 of FIG. 1 showed that $CO_2$ and bicarbonate were effectively removed. Polyols typically have a pKa on the order of 12 to 14, and are therefore are not effectively removed by mixed strong acid and base ion exchange resins. The concentration of recirculating polyol is preferably maintained as high as possible, the concentration being limited only by solubility or viscosity limits. In a preferred embodiment, solid polyol is maintained in polyol storage tank 25 in equilibrium with recirculating and deionized polyol reagent solution. This embodiment allows removal of one 3-way valve (valve 22 in FIG. 1) in the apparatus, but increases the risk of polyol precipitation in a small orifice, valve, or tube. Smaller injection volumes of higher concentration polyol solutions are desirable because aqueous samples analyzed will be less diluted by polyol injections.

Figure 6:
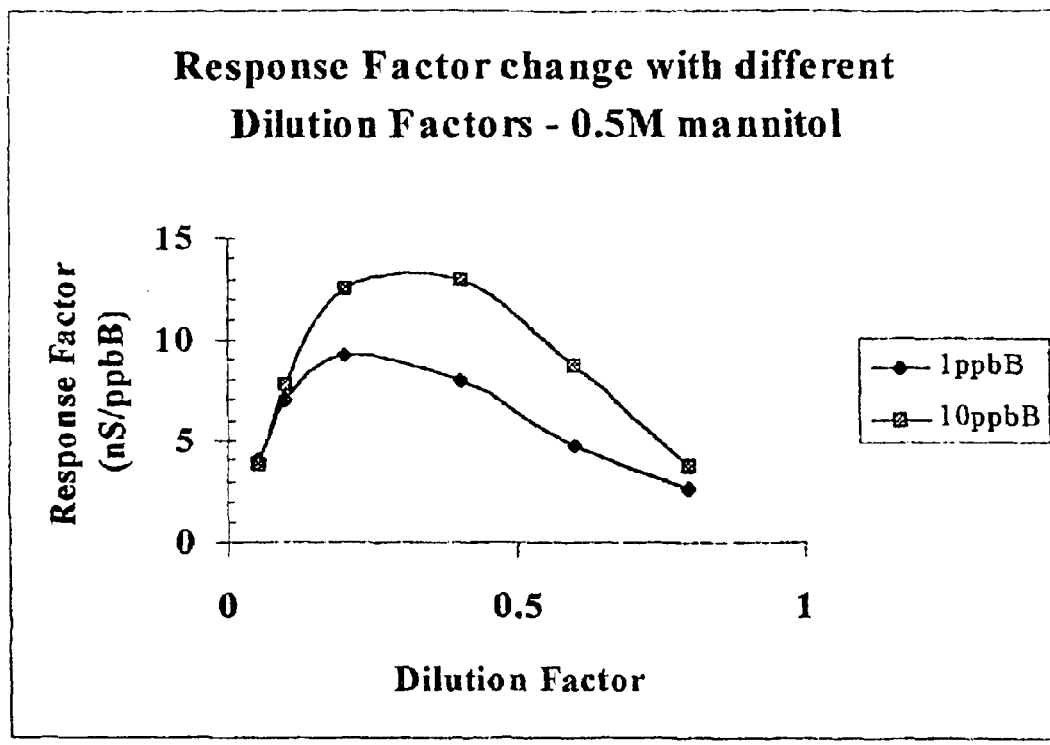
FIG. 6 is an illustrative graph of response factor plotted against dilution factor using 0.5M mannitol as polyol.
Figure 7:
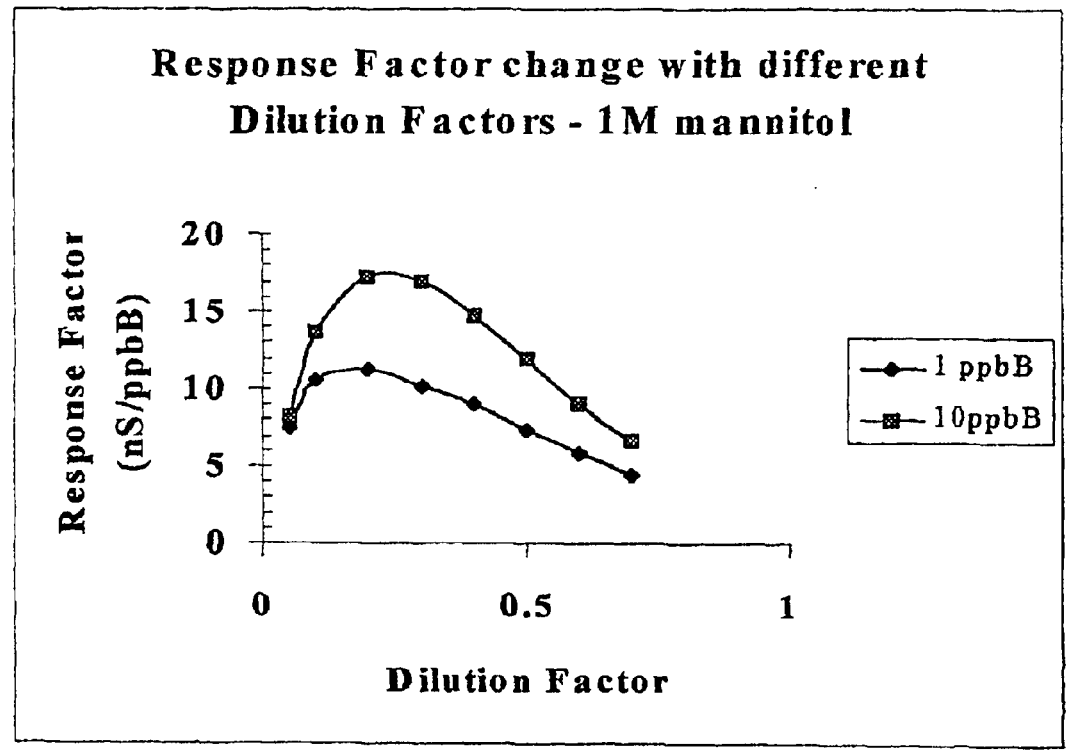
FIG. 7 is an illustrative graph of response factor plotted against dilution factor using 1M mannitol as polyol.

Still another novel aspect of the present invention involves maximizing conductivity peaks by optimizing polyol injection dilution factor. When a plug or aliquot of polyol reagent is injected into the delay coil (conduit 8 in FIG. 1), dispersion of polyol occurs through the delay or reaction coil extending to the conductivity and temperature measuring cell (reference number 23 in FIG. 1). This dispersion causes the concentration of polyol to decrease as it mixes into the sample. Such lowered polyol concentration, in turn, causes the conductivity peak to decrease. Dilution (D) can be modeled as $D=C_2/C_1$, where $C_1$ is the concentration of the original polyol solution and $C_2$ is the polyol concentration after dispersion. The concentration of boron in a boron-containing sample will obviously also be diluted as the polyol disperses in it. If the initial boron concentration is $B_r$, then the concentration of the diluted dispersion will be $(B_r)(1-D)$. If the initial concentration of polyol is L, then the concentration of the polyol after it has dispersed with the water sample at the conductivity cell will be (L)(D). When these equations are incorporated into the mathematical model of the chemistry, the optimum dilution factor can be calculated and plotted as shown in FIGS. 6 and 7, which show an optimum mixing ratio for a maximum response factor or sensitivity of the boron detector as a function of dilution factor. Such optimum dilution factor is an important feature of this invention.

Figure 8:
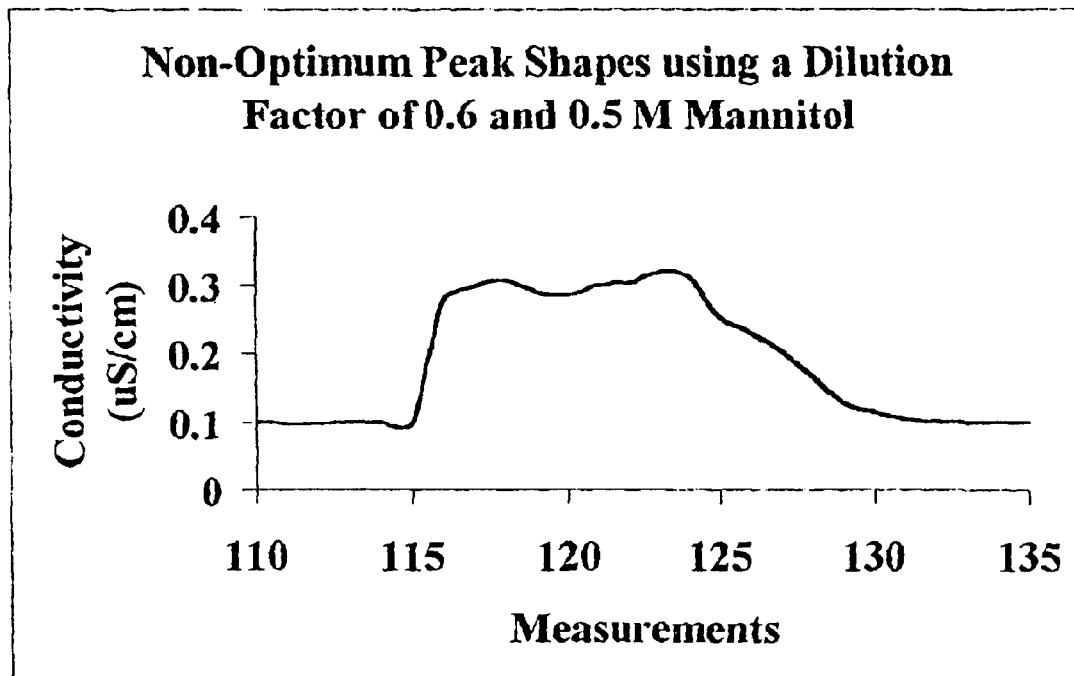
FIG. 8 is an illustrative graph for comparison purposes showing non-optimum peak shapes obtained using a non-optimum dilution factor and 0.5M mannitol (not part of this invention).
Figure 9:
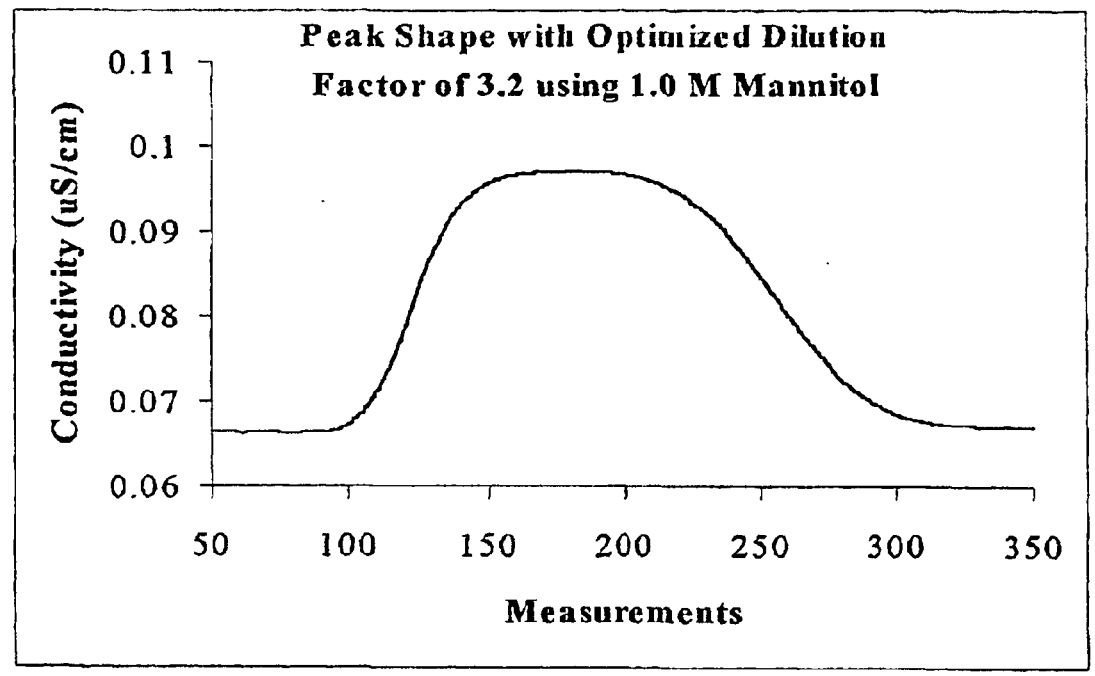
FIG. 9 is an illustrative graph showing an optimal peak shape obtained using an optimized dilution factor and 1M mannitol.

Injecting NaCl solution can be used directly to measure dilution factor, which can then be changed by adjusting the length and the internal diameter of the mixing coil empirically to provide the best mixing ratio for the particular concentration of the polyol. FIGS. 8 and 9 illustrate the effect dilution factor has on conductivity peak shape as a function of time. The poorly-defined peak shapes of FIG. 8 cause a decrease in precision, while the well-defined peak shape in FIG. 9 improves the precision of the boron analyzer.

Yet another novel aspect of the present invention involves maximizing conductivity increase by optimizing the concentration of polyol in polyol/boron-containing solutions. We have found that there is an optimum concentration for each polyol compound that gives a maximum conductivity increase when a complex is formed with boron. Additionally we have found that lower optimum mixing ratios lead to lower conductivity of the boron-free sample polyol solution reference measurement, thereby increasing accuracy and improving the limit of detection. Table 2 illustrates these relationships.

TABLE 2

Polyol Concentration and Optimum Mix Ratio

| Polyol | Concentration (Molarity) | Optimum Mix Ratio | Polyol-Boron Free Water Conductivity Increase, Compared to DI Water at 25° C. |
|---|---|---|---|
| Mannito | 1 M | 0.3 | 5.1 nano-Siemens |
| Sorbitol | 2 M | 0.1 | 3.5 nano-Siemens |

The ability of two very weakly acidic molecules, specifically boric acid and certain polyhydroxy ("polyol") compounds, to react and form a more highly dissociated acidic species, as illustrated below, is the basis for sensitive (preferably temperature corrected) conductometric detection of boron in deionized water according to this invention.

It is convenient to regard the reaction as one between metaborate anion, $BO_2^-$ and a diol as shown by the following equation in which it will be understood that at each junction of three lines there is a carbon (C) atom:

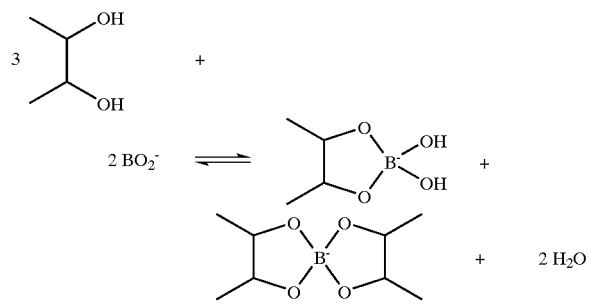

or symbolically $$3LH_2O+2B^- \leftrightarrows LB^-H_2O+L_2B^-+2H_2O$$

where

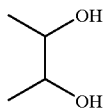

represents a polyol symbolically $C_2(OH)_2$ or $LH_2O$ where "L" represents the moiety "$C_2O$", i.e.,

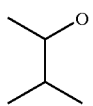

and "B" in the symbolic equation represents the metaborate anion $BO_2^-$.

Polyol molecules with a cis arrangement of hydroxyl groups usually provide the primary requisite to produce a large change in conductivity upon reaction with boric acid and/or its anions. Polyols effective in the present invention satisfy these requirements including but not limited to mannitol, sorbitol, xylitol, arabitol, alpha-mannitan, N-ethyl-meso tartarimide, cis-2-methyl-2,3-dihydroxytetramethylene sulfone, cis-1,4-dimethyl-2,3-dihydroxytetramethylene sulfone, hydrated triquinoyl (cyclohexanehexone hydrate), catechol, 3-nitrocatechol, pyrogallol and hexahydroxy benzene. Many other suitable polyols are well known in the art. See, for example, Steinberg ed. "Organo-boron Chemistry," pages 661 to 675. Of the polyols listed in Steinberg, those having a Δ (delta) of at least about 100 at a concentration of about 0.5 molar are preferred, those having a Δ of at least about 300 at such concentration are more preferred, and those have a Δ of at least about 600 at such concentration are most preferred, where Δ is defined in Steinberg as: conductivity of polyol-boric acid solution minus the sum of the conductivities of the individual polyol and boric acid solutions in Kohlrausch-Holburn units×10$^6$.

For use with the boron measurement system of this invention, it is preferable to select a polyol which has a very low inherent (intrinsic) electrical conductivity in solution and a high association constant for boric acid and/or its anions. Such property lowers background electrical conductivity and improves the low end detection limit. It is also preferable to use a polyol which has a high solubility in water, preferably at least 0.1 gram moles/liter, more preferably at least 0.3 gram moles/liter, most preferably at least 0.5 gram moles/liter. Especially preferred are polyols having a solubility of 1 gram mole/liter or more. As the concentration of polyol increases, response factor and low limit of detection improve when, as is preferred, the polyol is intrinsic, that is substantially free of any ions other than those produced by the intrinsic (inherent) dissociation of the polyol per se. Such extraneous (foreign) ions are preferably present at concentrations of about one-tenth or less than ions produced by such intrinsic dissociation of polyol.

The polyol should also be inexpensive, non-toxic and stable.

The chemical reactions which underlie the boron measurement system of this invention can be modeled to predict, at least qualitatively, conductivity response from addition of polyol to boron-containing water as functions of polyol and boron concentrations. An inverse equation can be used to calculate/estimate boron concentration based on conductivity increase of polyol/boron containing water compared to a polyol-boron-free sample of such water.

The fundamental equations may be written:

$$HBO_2 \leftrightarrows BO_2^- + H^+ \text{ or symbolically } BH \leftrightarrows B^- + H^+ \qquad 1.$$

For the above, it has been found convenient to represent boric acid as metaboric acid $HBO_2$ and its anion as the metaborate anion $BO_2^-$. Alternative representations include:

$$H_3BO_3 \leftrightarrows H_2BO_3^- + H^+ \qquad (b)$$

$$B(OH)_3 + H_2O \leftrightarrows B(OH)_4^- + H^+ \qquad (c)$$

$$B(OH)_3 + 2H_2O \leftrightarrows B(OH)_4^- + H_3O^+ \qquad (d)$$

etc. One of ordinary skill in the art can choose whichever of the above (or some permutation) is most comfortable.

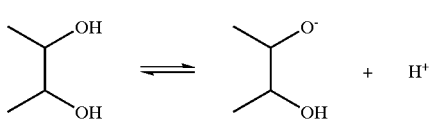

2.

or symbolically $$C_2(OH)_2 \leftrightarrows C_2O_2H^- + H^+ \text{ or preferably}$$

$$LH_2O \leftrightarrows LOH^- + H^+ \text{ where "L" is a symbol for "}C_2O\text{"}.$$

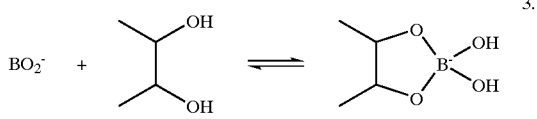　3.

or symbolically

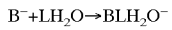　10

The above equation illustrates the convenience of assuming that the species which reacts with polyol is metaborate anion $BO_2^-$. One of ordinary skill in the art can, if he or she prefers, write equation 3 assuming $H_2BO_3^-$ or $B(OH)_4^-$ instead of $BO_2^-$, in the former case adding 1 $H_2O$ as an additional product of the reaction and in the latter case adding 2 $H_2O$.

Equation 3, written with borate anions, produces no additional $H^+$, the overall reaction scheme assuming that only Equation 1 above (or one of its equivalents) produces $H^+$, Equation 1 being driven to the right by the addition of polyol, removing borate according to Equation 3. If preferred, one can condense Equations 1 and 3 together writing

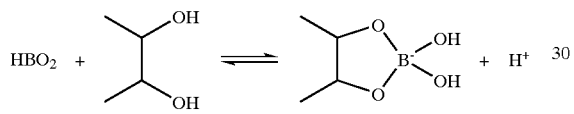

or any of its equivalents or symbolic equations.

4.

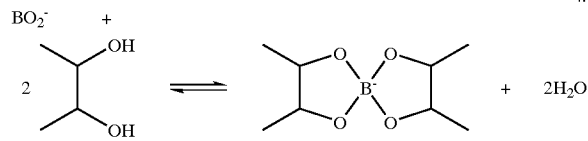

or symbolically:

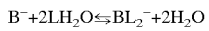

Note, based on the assumption made in writing Equation 1 above, Equation 4 also does not produce $H^+$ and instead serves also to drive Equation 1 to the right by removing $BO_2^-$.

$H_2O \rightleftharpoons H^+ + OH^-$ or if one prefers:

$2H_2O \rightleftharpoons H_3O^+ + OH^-$　5.

In the above symbolic equations:
BH=neutral metaboric acid, $HBO_2$
$B^-$=metaborate anion, $BO_2^-$
$LH_2O$=polyol,

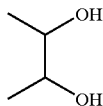

$LOH^-$=polyol anion,

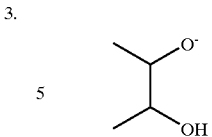

$BLH_2O^-$=boron polyol complex,

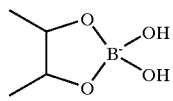

$BL_2^-$=boron-polyol complex,

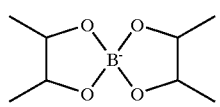

$B_t$=total boron
$H^+$=hydrogen ion=hydronium ion=$H_3O^+$
$OH^-$=hydroxide anion.

The reaction equilibria, mass balances, charge balances and conductivity equations used to model this system are:

$$K_a = \frac{[B^-][H^+]}{[BH]} \quad 6.$$

$$K_L = \frac{[LOH^-][H^+]}{[LH_2O]} \quad 7.$$

$$K_1 = \frac{[BLH_2O^-]}{[B^-][LH_2O]} \quad 8.$$

$$K_2 = \frac{[BL_2^-]}{[B^-][LH_2O]^2} \frac{(K_2')}{(=[H_2O]^2)} \quad 9.$$

Where $K_2$ includes the inverse square of the activity of water as indicated in parentheses on the right hand side of Equation 9. It is estimated that in a 1 molar solution of mannitol, the activity of water is almost that of pure water. However at higher concentrations of polyol, also useful in this invention, the activity of water may be substantially reduced.

$K_W=[H^+][OH^-](=K_W'[H_2O])$ or
$K_W=[H_3O^+][OH^-](=K_W''[H_2O]^2)$　10.
$(B_t)=(B^-)+(BLH_2^-)+(BL_2^-)+(BH)$　11.
$(H^+)=(B^-)+(BLH_2O^-)+(BL_2^-)+(LOH^-)+(OH^-)$　12.

In the above "[ ]" indicates activities and "( )" indicates concentrations. It has already been pointed out that in many (but not all) cases of interest it is probably reasonable to assume that activities and concentrations are substantially equal.

$S=\{(H^+)\char`\^_{H+}+(OH^-)\char`\^_{OH-}+(BLH_2O^-)\char`\^_{BLH2O-}+(BL_2^-)\char`\^_{BL2-}$
$+(B^-)\char`\^_{B-}+(LO_2^{14-})\char`\^_{LO2H-}\}$　13.

The meaning of the third term in the above equation is: "the concentration of $BLH_2O^{31}$ multiplied by the molar conductance of $BLH_2O^-$, that is by ^ subscript $BLH_2O^-$." The other terms in the above equation have similar meanings. In most published tables of equivalent conductivity ("^" in the above), the values are in Siemens-cm$^2$/gram-equivalent, in which case the concentrations "( )" must be in gram-equivalents/cm$^3$ and the specific conductivity "S" will then be in Siemens/cm. Some such tables however list molar conductivities, i.e., Siemens-cm$^2$/gram mole. One skilled in the art should be alert to the possibility that different units are used.

It appears that the various equivalent conductivities at infinite dilution in Equation 13 are about as follows, $LH_2O=$ mannitol or sorbitol:

| | |
|---|---|
| $\hat{}$H+ | 349.8 |
| $\hat{}$OH− | 198.3 |
| $\hat{}$LO2H− | 24 (approx.) |
| $\hat{}$B− | 70 (approx.) |
| $\hat{}$BLH2O− | 23 (approx.) |
| $\hat{}$BL2− | 16 (approx.) | all in Siemens-cm$^2$/grain-equivalent at infinite dilution at 25° C. They must be corrected for viscosity due to polyol, which for mannitol or sorbitol is approximately:

| Molarity | Viscosity centipoise |
|---|---|
| 1 | 1.88 |
| 0.9 | 1.76 |
| 0.8 | 1.65 |
| 0.7 | 1.55 |
| 0.6 | 1.46 |
| 0.5 | 1.37 |
| 0.4 | 1.29 |
| 0.3 | 1.22 |
| 0.2 | 1.15 |
| 0.1 | 1.09 |

In the above, $K_a$, $K_L$, $K_1$, $K_2$, $K_W$, (equilibrium constants) are a function of temperature, correction for which can be incorporated in a suitable overall temperature correction. The equivalent conductances are also a function of temperature, correction for which can also be included in such overall temperature correction.

Methods well known in the art for many years can be readily used by one of ordinary skill in the art to measure the necessary K's, $\hat{}$'s and viscosity in any solution of any polyol. Preferably such measurements are made using such polyol at whatever concentration is intended to be used. Alternatively, a series of measurements of conductivity (preferably also of pH) will permit calculation of the necessary constants and their variations with polyol concentration and temperature.

The foregoing equations can be rearranged to calculate boron concentrations in the samples as a function of conductivity response to a polyol/boron-containing sample, conductivity response to a polyol/boron-free sample, temperature, dilution factor, and polyol concentration. Note that Equation 13 above requires that the polyol and the water sample be free of all other ions.

Figure 10:
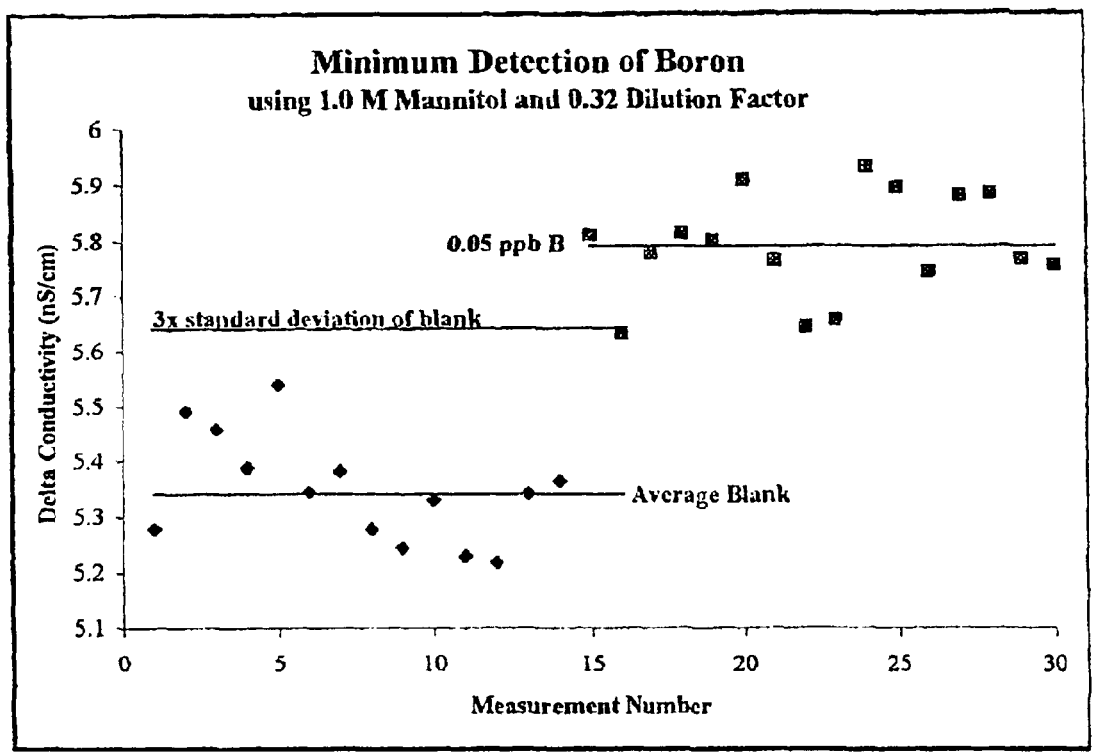
FIG. 10 is an illustrative graph showing boron detection levels using 1M mannitol and a 0.32 dilution factor.

One of the principal benefits of the boron measurement system of this invention is a dramatic improvement in the smallest concentration of boron that can be easily detected and accurately measured. Using an above-described preferred embodiment of this invention in conjunction with polyol/boron-free sample conductivity background correction and high concentrations of intrinsic polyol injected in very small aliquots into boron-containing and boron-free samples allows measurement of boron at concentrations one to three orders of magnitude lower than prior art apparatus and methods using polyol/boron conductivity detection. FIG. 10 shows a typical limit of detection for a boron analyzer according to this invention to be as low as about 50 parts per trillion (0.05 ppb) as boron. Additional optimization of the boron analyzer in accordance with the teachings of this application further lowers the limit of detection to as low as 1–10 parts per trillion as boron, a practical low end range being about 1–50 parts per trillion B.

Figure 11:
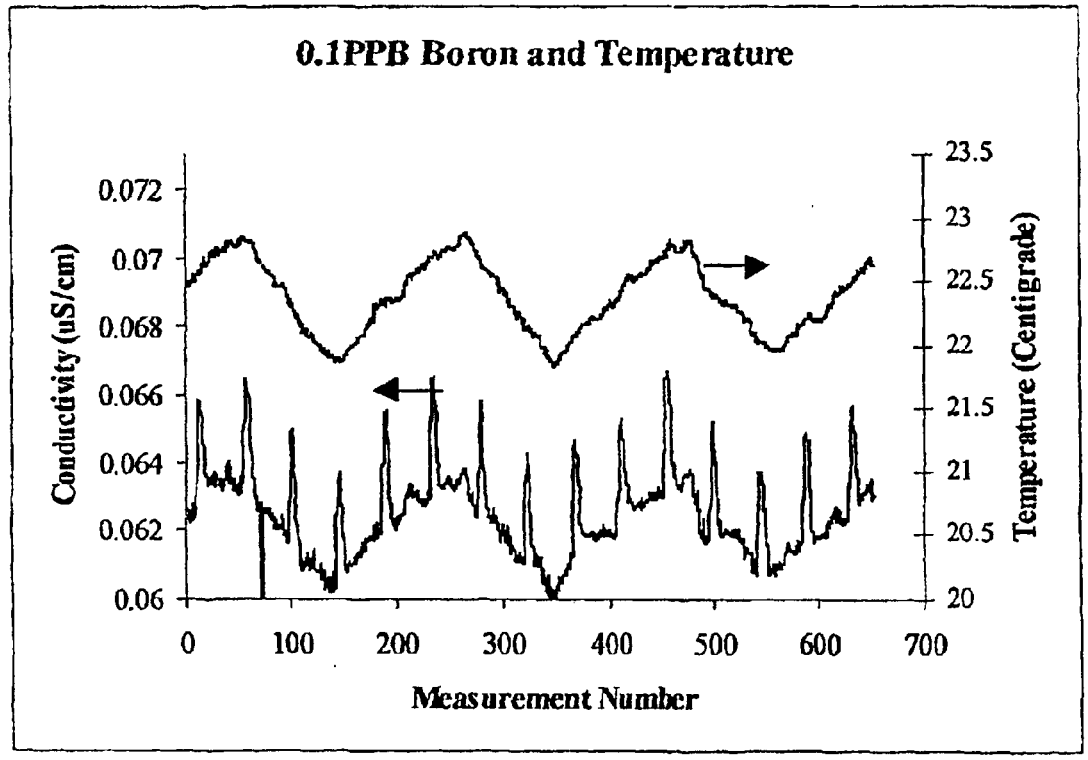
FIG. 11 is an illustrative graph showing conductivity and temperature plots for a 0.1 ppb boron concentration.

Accurate boron concentration measurements based on electrical conductivity require compensation for temperature. This principle is even more critical for very low level boron measurements. The chemical equilibria, acid dissociation constants, and the molar conductances of each ion are all affected by temperature. FIG. 11 shows the strong effect of temperature variations on the raw conductivity output during a 0.1 ppb boron injection into a boron containing water sample. The level of conductivity variation from thermal changes is on the same order as the conductivity signal induced from polyol injection and reaction with low concentrations of boron. FIG. 11 clearly illustrates the temperature sensitivity of polyol/boron containing samples. The same figure highlights the need for a temperature correction procedure appropriate for the chosen boron analysis to achieve accurate low level boron concentration analysis.

Three methods are preferably used to control effects of changing temperature on conductometric polyol/boron analysis measurements of this invention. The first method requires fixing the temperature at a precise controlled level. This makes the conductometric boron detection independent of changing or different sample and ambient air temperatures. Such method benefits greatly from the lower thermal mass of a miniaturized apparatus such as practiced in this invention. The second method utilizes a mathematical model which describes the kinetics and chemical reactions as a function of temperature. Fluid dynamic and chemometric models that accurately represent the functionality of the measurement process can predict and correct for changes in temperature. A third preferred method measures the response of a boron detector to accurate concentration standards at various temperatures and then fits this empirical data to a mathematical function that inputs temperature and raw conductivity and outputs a temperature-corrected boron concentration. When such third method is applied to the differential conductivity signal (conductivity of the polyol/boron-containing sample minus conductivity of the polyol/boron-free sample), the correction becomes automatic due to the cancellation of the temperature sensitive conductivity of the water and polyol mixture. We have determined that the boron/polyol complex conductivity is not very dependent on the steady-state temperature actually used. In this case, little or no thermal correction is needed over the typical steady-state temperature range of 25° C. to 45° C.

It will be apparent to those skilled in the art that other changes and modifications may be made in the above-described apparatus and methods for low level boron detection and measurement without departing from the scope of the invention herein, and it is intended that all matter contained in the above description shall be interpreted in an illustrative and not a limiting sense.

What is claimed is:

1. Apparatus for measurement of boron at very low concentration in water or other solvent comprising:
    (a) a source of a sample of said water or other solvent which may contain boron;
    (b) a source of a sample of said water or other solvent which is substantially free of boron;
    (c) a source of substantially intrinsic polyol solution, said polyol capable of forming a complex with boric acid and/or anions of boric acid;

(d) a contacting system for: (i) contacting a portion of said intrinsic polyol solution intermittently with said sample of said water or other solvent which may contain boron thereby forming a first volume of liquid comprising said polyol and said water or solvent; and (ii) intermittently contacting a portion of said intrinsic polyol solution with said sample of said water or other solvent substantially free of boron thereby forming a second volume of liquid comprising said polyol and said water or other solvent substantially free of boron;

(e) a conductance measuring unit for measuring electrical conductance of said first volume of liquid and, alternatively, of said second volume of liquid; and, (f) a correlating system for correlating boron concentration in said water or other solvent with said conductance of said first volume of liquid and said conductance of said second volume of liquid.

2. Apparatus according to claim 1 in which said contacting system comprises at least one element selected from the group consisting of:
an injection loop;
a multiport injection valve;
a delay line; and,
a semipermeable membrane juxtaposed on a first face of said contacting system by a flow path for said sample of said water or other solvent which may contain boron, alternatively for said sample of said water or other solvent substantially free of boron, and juxtaposed on a second face of said contacting system by a flow path for said substantially intrinsic polyol solution, said semipermeable membrane being substantially permeable to boric acid and/or anions of boric acid and substantially impermeable to said polyol, said membrane thereby forming said first volume of liquid on said second face or, alternatively, said second volume of liquid on said second face.

3. Apparatus according to claim 1 which said source of substantially intrinsic polyol solution comprises cation exchange resin in acid from and an anion exchange resin in base form.

4. Apparatus according to claim 1 in which said source of substantially intrinsic polyol solution comprises boron specific exchange resin.

5. Apparatus according to claim 1 in which said source of substantially intrinsic polyol solution comprises a concentration control subsystem for maintaining a predetermined concentration of polyol.

6. Apparatus according to claim 1 in which said polyol has a $\Delta$ of at least about 100 at a concentration of about 0.5 molar where $\Delta$ is the conductivity of polyol-boric acid solution minus the sum of the conductivities of separate polyol and boric acid solutions in Kohlraush-Holborn units $\times 10_6$.

7. Apparatus according to claim 6 in which said polyol has a $\Delta$ of at least about 300 at a concentration of about 0.5 molar.

8. Apparatus according to claim 6 in which said polyol has a $\Delta$ of at least about 600 at a concentration of about 0.5 molar.

9. Apparatus according to claim 1 in which said source of a sample of said water or other solvent includes an electrolyte removal system for removing from said sample electrolytes more strongly ionized than is boric acid in neutral solutions, said electrolyte removal system substantially not removing boric acid and/or anions of boric acid.

10. Apparatus according to claim 1 in which said source of a sample of said water or other solvent includes an interfering substance removal system for removing from said sample one or more substances which interfere with said measurement of boron, said interfering substance removal system substantially not removing boric acid and/or anions of boric acid.

11. Apparatus according to claim 1 in which said conductance measuring unit is a bipolar pulse conductivity measuring element.

12. Apparatus according to claim 1 in which said conductance measuring unit includes electrodes.

13. Apparatus according to claim 1 in which said conductance measuring unit does not include electrodes, 14. Apparatus according to claim 1 in which said conductance measuring unit includes a temperature measurement clement for measuring temperature.

15. Apparatus according to claim 1 in which said conductance measuring unit further comprises a temperature control system for controlling the temperature of said unit to a predetermined temperature.

16. An apparatus according to claim 1 for accurate measurement of boron in an aqueous solution at a very low concentration of about 0.001 ppb to about 1000 ppb as boron, said apparatus comprising in combination: (a) a sample injection system comprising a multi-port valve assembly capable of receiving at least two liquid feeds from at least two valve input conduits, of outputting liquid streams to at least two valve output conduits, and of alternatively channeling one or another of the two liquid feeds to an injection loop for circulating said one or another liquid feed alternatively to one or another of the valve output conduits; (b) a sample water delivery system for alternatively supplying a boron-containing sample water portion or a born-free sample water portion to said sample injection system; (c) a polyol supply system the supplying a portion of a polyol solution to said sample injection system; (d) a conductance cell for measuring the electrical conductance of a liquid; and (e) a conduit for carrying fluid from said injection loop of said sample injection system to said conductance cell.

17. An apparatus according to claim 16 comprising a fluid flow control device downstream from said conductivity cell.

18. An apparatus according to 16 wherein said sample water delivery system comprises a sample water inlet; conduits for channeling a sample from said sample water inlet either through a boron-removing resin, or alternatively, so as to bypass said boron-removing resin; at least a valve for controlling whether said sample passes through or bypasses said boron-removing resin; and, a fluid conduit connecting said sample supply system to an input conduit of said injection system.

19. An apparatus according to claim 16 wherein said polyol supply system comprises a reservoir of concentrated polyol solution; a conduit system for circulating said polyol solution through a resin bed to remove ionic contaminants; and a liquid conduit connecting said polyol supply system to an input conduit of said injection system.

20. An apparatus according to claim 19 further comprising a liquid conduit connecting an output conduit of said injection system to said polyol supply system.

21. A method for measurement of boron at very low concentrations in water or other solvent, said method comprising providing an apparatus which comprises:
(i) a source of a sample of said water or other solvent which may contain boron;
(ii) a source of a sample of said water or other solvent which is substantially free of boron;
(iii) a source of substantially intrinsic polyol solution, said polyol capable of forming a complex with boric acid and/or anions of boric acid;

(iv) a contacting system for: (i) contacting a portion of said intrinsic polyol solution intermittently with said sample of said water or other solvent which may contain boron thereby forming a first volume of liquid comprising said polyol and said water or solvent; and (ii) intermittently contacting a portion of said intrinsic polyol solution with said sample of said water or other solvent substantially free of boron thereby forming a second volume of liquid comprising said polyol and said water or other solvent substantially free of boron;

(v) a conductance measuring unit for measuring electrical conductance of said first volume of liquid and, alternatively, of said second volume of liquid; and, (vi) a correlating system for correlating boron concentration in said water or other solvent with said conductance of said first volume of liquid and said conductance of said second volume of liquid;

said method comprising the further steps of:

(a) providing a flowing sample of said water other solvent which may contain boron;

(b) contacting a portion of said intrinsic polyol solution intermittently with said flowing sample which may contain boron to form said first volume of liquid;

(c) measuring electrical conductance of said first volume of liquid;

(d) intermittently providing a flowing sample of said water or other solvent which is substantially free of boron;

(e) contacting a portion of said intrinsic polyol solution with said flowing sample which is substantially free of boron to form said second volume of liquid;

(f) measuring electrical conductance of said second volume of liquid; and, (g) correlating boron concentration in said water or other solvent with the electrical conductance of said first volume off liquid and the electrical conductance of said second volume of liquid.

22. A method according to 21 further comprising the step of displaying and/or recording said correlated boron concentration.

23. A method according to claim 21 or 22 in which said contacting system comprises at least one element selected from the group consisting of;

an injection loop;

a multiport injection valve;

a delay line; and, a semipermeable membrane juxtaposed on a first face of said contacting system by a how path for said sample of said water or other solvent which may contain boron, alternatively for said sample of said water or other solvent substantially free of boron, and juxtaposed on a second face of said contacting system by a flow path for said substantially intrinsic polyol solution, said semipermeable membrane being substantially permeable to boric acid and/or anions of boric acid and substantially impermeable to said polyol, said membrane thereby forming said first volume of liquid on said second face or, alternatively, said second volume of liquid on said second face.

24. A method according to either of claim 21 or 22 in which said source of substantially intrinsic polyol solution comprises cation exchange resin in acid form and anion exchange resin in base form.

25. A method according to either of claim 21 or 22 in which said source of substantially intrinsic polyol solution comprises boron specific exchange resin.

26. A method according to either of claim 21 or 22 in which said source of substantially intrinsic polyol solution comprises means for maintaining a predetermined concentration of polyol.

27. A method according to either of claim 21 or 22 in which said polyol has a $\Delta$ of at least about 100 at a concentration of about 0.5 molar where $\Delta$ is die conductivity of polyol-boric acid solution minus the sum of the conductivities of polyol and boric acid solutions per se in Kohlrauth-Holborn units $\times 10^6$.

28. A method according to claim 27 which said polyol has a $\Delta$ of at least about 300 at a concentration of about 0.5 molar.

29. A method according to claim 27 in which said polyol has a $\Delta$ of at least about 600 at a concentration of about 0.5 molar.

30. A method according to either of claim 21 or 22 in which said source of a sample of said water or other solvent includes an electrolyte removal system for removing from said sample electrolytes more strongly ionized than is boric acid in neutral solutions, said electrolyte removal system substantially not removing boric acid and/or anions of boric acid.

31. A method according to either of claim 21 or 22 in which said source of a sample of said water or other solvent includes an interfering substance removal system for removing from said sample one or more substances which interfere with said measurement of boron, said interfering substance removal system substantially not removing boric acid and/or anions of boric acid.

32. A method according to either of claim 21 or 22 in which said conductance measuring unit is a bipolar pulse conductivity measuring device.

33. A method according to either of claim 21 or 22 in which said conductance measuring unit includes electrodes.

34. A method according to either of claim 21 or 22 in which said conductance measuring unit does not include electrodes.

35. A method according to either of claim 21 or 22 in which said conductance measuring unit includes a temperature measurement element for measuring temperature.

36. A method according to either of claim 21 or 22 in which said conductance measuring unit includes a temperature control element for controlling temperature.

37. A method for measurement of boron in an aqueous solution at a very low concentration of about 0.001 ppb to about 1000 ppb as boron comprising the steps of: (a) adding to a small aliquot injection of a polyol solution a boron containing sample water portion, and measuring conductance of the resulting polyol/boron sample water solution; (b) adding to a small aliquot injection of the polyol solution a substantially boron-free sample water portion, and measuring conductance of the resulting polyo/boron-free sample water solution; (c) determining a conductance differential based on the difference between the conductance of the polyol/boron-containing sample water solution and the conductance of the polyol/boron-free sample water solution; and (d) relating said conductance differential to the concentration of boron in the boron-containing sample water portion.

38. A method according to claim 37 wherein said polyol solution has a concentration of at least 0.05 polyol/l 39. A method according to claim 37 further wherein the volume of each said small aliquot injection of a polyol solution is not more than about 50 microliters.

40. A method according to claim 37 further comprising the step of passing said polyol solution through a delonization resin prior to injection into a boron-containing or substantially boron-free sample water portion.

41. A method according to claim 37 further comprising the stop of passing a portion of a boron-containing water sample through a boron-removal resin to obtain said boron-free sample water portion.

42. A method according to claim 37 further comprising the steps of adjusting a polyol injection dilution factor and maximizing any conductance peaks for polyol/boron-containing and polyol/boron-free sample water solutions by optimizing said polyol injection dilution factor.

43. A method according to claim 37 further comprising the steps of adjusting a conductance response and maximizing said conductance response of the polyo/boron-containing sample water solution by optimizing the concentration of polyol in said polyol solution.

* * * * *